(12) United States Patent
Aw et al.

(10) Patent No.: US 11,174,505 B2
(45) Date of Patent: Nov. 16, 2021

(54) SIMPLE ONE-STEP REAL-TIME MOLECULAR SYSTEM FOR MICRORNA DETECTION

(71) Applicant: AGENCY FOR SCIENCE, TECHNOLOGY AND RESEARCH, Singapore (SG)

(72) Inventors: Sherry Aw, Singapore (SG); Yin Nah Teo, Singapore (SG); Stephen Michael Cohen, Singapore (SG); Melissa Xue Mei Tang, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 264 days.

(21) Appl. No.: 16/079,992

(22) PCT Filed: Feb. 24, 2017

(86) PCT No.: PCT/SG2017/050086
§ 371 (c)(1),
(2) Date: Aug. 24, 2018

(87) PCT Pub. No.: WO2017/146653
PCT Pub. Date: Aug. 31, 2017

(65) Prior Publication Data
US 2019/0382830 A1    Dec. 19, 2019

(30) Foreign Application Priority Data

Feb. 24, 2016   (SG) .......................... 10201601384T

(51) Int. Cl.
*C12Q 1/6816*    (2018.01)

(52) U.S. Cl.
CPC ..... *C12Q 1/6816* (2013.01); *C12Q 2600/178* (2013.01)

(58) Field of Classification Search
CPC ..................... C12Q 1/6816; C12Q 2600/178
See application file for complete search history.

(56) References Cited

U.S. PATENT DOCUMENTS

2015/0141282 A1    5/2015   Jaffrey et al.

FOREIGN PATENT DOCUMENTS

EP            0745690 A2     12/1996
WO    WO 2013/016694 A1      1/2013

OTHER PUBLICATIONS

Bhadra, Sanchita; et al.; "Spinach Molecular Beacon Triggered by Strand Displacement"; RNA, vol. 20. 1183-1194, (2014); 12 pp.
Brennecke, Julius; et al.; bantam Encodes a Developmentally Regulated microRNA that Controls Cell Proliferation and Regulates the Proapoptotic Gene hid in *Drosophila*; Cell. 113. 25-36, (2003); 12pp.
DiLeva, Gianpiero; et al., miRNA Profiling of Cancer. Curr Opin Genet. Dev., 23, 3-11. (2013); 14 pp.

(Continued)

*Primary Examiner* — Joseph G. Dauner
(74) *Attorney, Agent, or Firm* — Womble Bond Dickinson (US) LLP

(57) ABSTRACT

The present application discloses an isolated nucleic acid sequence for detecting the presence of a target nucleic acid sequence, a ribozyme for detecting the presence of a target nucleic acid sequence and uses thereof.

14 Claims, 21 Drawing Sheets

Specification includes a Sequence Listing.

(56) References Cited

OTHER PUBLICATIONS

Dong, Haifeng; et al.; "The use of Polyethylenimine-grafted Graphene Nanoribbon for Cellular Delivery of Locked Nucleic Acid Modified Molecular Beacon for Recognition of MicroRNA" Biomaterials. 32, (2011) 3875-3882. 10 pp.

Ebert, Margaret; et al.; Roles for microRNAs in Conferring Robustness to Biological Processes. Cell, 149, 515-524. (2012); 20 pp.

Esteller, Manel; "Non-coding RNAs in Human Disease"; Nature Reviews Genetics 12, 861-874, (2011); 14 pp.

Farazi, Thalia; et al. "MicroRNA Sequence and Expression Analysis in Breast Tumors by Deep Sequencing"; Cancer Research; 71(13): 4443-4453; (2011); 16 pp.

Herranz, Hector; et al.; MicroRNAs and Gene Regulatory Networks: Managing the Impact of Noise in Biological Systems. Genes & Dev., 24, 1339-1344; (2010); 6 pp.

Huang, Hao; et al.; A G-quadruplex-containing RNA Activates Fluorescence in a GFP-like Fluorophore. Nat. Chem. Biol. 686-691; (2014); 22 pp.

Maciotta, Simona; et al.; "The Involvement of MicroRNAs in Neurodegenerative Diseases". Frontier Cellular Neuroscience., 7, 265; (2013); 17 pp.

Mendell, Joshua T.; et al; "MicroRNAs in Stress Signaling and Human Disease"; Cell 148(6): 1172-1187; (2012); 26 pp.

Paige, Jeremy S.; et al.; "RNA Mimics of Green Fluorescent Protein"; Science, 333(6042) 642-646; (2011); 14 pp.

Paige, Jeremy S.; et al; "Fluorescence imaging of cellular metabolites with RNA"; Science, 335. (6073) 1194; 2012; 3 pp.

Rooij, Eva; "The Art MicroRNA Research"; Circulation Research (2011);108:219-234; 16 pp.

Sayed, Danish; et al.; "Micrornas in Development and Disease"; Physio/ Rev 91: 827-8871 (2011); 61 pp.

Winter, Julia; et al.; "Many Roads to Maturity: MicroRNA Biogenesis Pathways and their Regulation"; Nature Cell Biology 11, 228 234; (2009); 8 pp.

Yoo, Byunghee; et al.; Detection of miRNA Expression in Intact Cells Using Activatable Sensor oligonucleotides. Chem. Biol., 21(2), 199-204; (2014); 13 pp.

Zhou, Yuntao; et al.; "A Dumbbell Probe-Mediated Rolling Circle Amplification Strategy for Highly Sensitive MicroRNA Detection"; Nucleic Acids Res., vol. 38, No. 15; (2010); 5 pp.

PCT Notification of the "International Preliminary Report on Patentability" for Counterpart PCT Application No. PCT/SG2017/050086; date of completion, May 4, 2017; 7 pp.

IP Office of Singapore—Notification of Transmittal of the International Search Report & the Written Opinion of the International Searching Authority, or the Declaration, with the International Search Report & Written Opinion dated May 9, 2017 for International Application No. PCT/SG2017/050086 (13 pgs).

Aw, S.S., et al., "A Conformation-induced Fluorescence Method for microRNA Detection." Nucleic Acids Research, Mar. 6, 2016, vol. 44, No. 10, pp. e92:1-9.

Ketterer, S., et al., "Systematic Reconstruction of Binding and Stability Landscapes of the Fluorgenic Aptamer Spinach." *Nucleic Acids Research*, Sep. 22, 2015, vol. 43, No. 19, pp. 9564-9572.

Song, W., et al., "Plug-and-Play Fluorophores Extend the Spectral Properties of Spinach." *J. Am. Chem. Soc.*, Jan. 6, 2014, vol. 136, No. 4, pp. 1198-1201.

Warner, K. D., et al., "Structural Basis for Activity of Highly Efficient RNA Mimics of Green Fluorescent Protein." *Nature Structural & Molecular Biology*, Jul. 15, 2014, vol. 21, No. 8, pp. 658-665.

Duan et al., "Quadratic isothermal amplification for the detection of microRNA" Nature Protocols, vol. 9, Feb. 13, 2014, pp. 597-607.

Jia et al., "Ultrasensitive detection of microRNAs by exponential isothermal amplification" Angewandte Chemie International Edition, vol. 49 Issue 32, Jul. 22, 2010, pp. 5498-5501.

Li et al., "MicroRNA detection by microarray" Analytical and Bioanalytical Chemistry, vol. 394, Jan. 9, 2009, pp. 1117-1124.

Thomson et al., "A custom microarray platform for analysis of microRNA gene expression" Nature Methods, vol. 1 No. 1, Sep. 29, 2004, pp. 47-53.

Kloosterman et al., "In situ detection of miRNAs in animal embryos using LNA-modified oligonucleotide probes" Nature Methods, vol. 3 No. 1, Jan. 2006, pp. 27-29.

Hwang et al., "Smart magnetic fluorescent nanoparticle imaging probes to monitor microRNAs" Small, vol. 6 Issue 1, Dec. 28, 2009, pp. 81-88.

Rogers et al., "Fluorescent monitoring of RNA assembly and processing using the split-spinach aptamer" ACS Synthetic Biology, vol. 4 No. 2, May 8, 2014, pp. 162-166.

Kang et al., "Molecular beacon-based bioimaging of multiple microRNAs during myogenesis" Biomaterials, vol. 32 Issue 7, Dec. 3, 2010, pp. 1915-1922.

A

B

| miRNA | Sequence |
|---|---|
| Bantam5p miRNA | CCGGUUUUCGAUUUGGUUUGACU (SEQ ID NO.: 2599) |
| Bantam5p_2nt (2nt mutation in seed) | CGGCUUUUCGAUUUGGUUUGACU (SEQ ID NO.: 2602) |
| Bantam5p_3nt (3nt mutation in seed) | CGGCUUAUCGAUUUGGUUUGACU (SEQ ID NO.: 2603) |

| miRNA | Sequence |
|---|---|
| bantam-5p | CCGGUUUUCGAUUUGGUUUGACU (SEQ ID NO: 2599) |
| bantam-5p (3nt mutation in seed) | CGGCUUAUCGAUUUGGUUUGACU (SEQ ID NO: 2603) |
| miR-263a | AAUGGCACUGGAAGAAUUCACGGG (SEQ ID NO: 2609) |
| miR263a (3nt mutation in seed) | AAACGGACUGGAAGAAUUCACGGG (SEQ ID NO: 2610) |
| miR-1000 | AUAUUGUCCUGUCACAGCAGU (SEQ ID NO: 2611) |
| miR1000-5p (3nt mutation in seed) | AUUAUCUCCUGUCACAGCAGU (SEQ ID NO: 2612) |

C

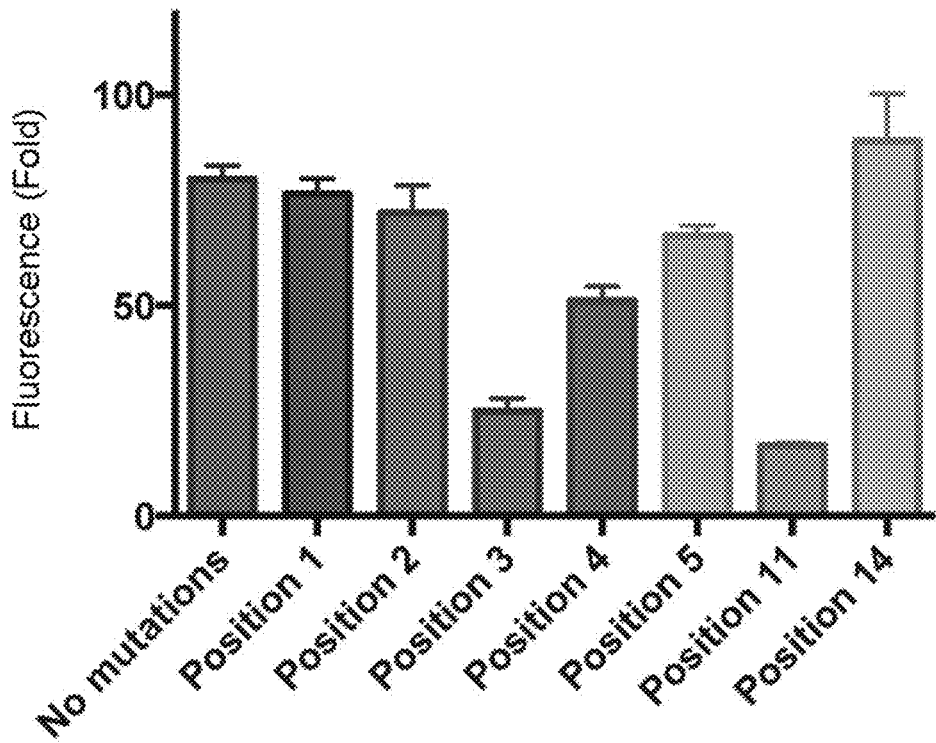

| miRNA | Sequence |
|---|---|
| bantam-5p_Mut Position 1 | GCGGUUUUCGAUUUGGUUUGACU (SEQ ID NO: 2604) |
| bantam-5p_Mut Position 2 | CGGGUUUUCGAUUUGGUUUGACU (SEQ ID NO: 2605) |
| bantam-5p_Mut Position 3 | CCCGUUUUCGAUUUGGUUUGACU (SEQ ID NO: 2606) |
| bantam-5p_Mut Position 4 | CCGCUUUUCGAUUUGGUUUGACU (SEQ ID NO: 2607) |
| bantam-5p_Mut Position 5 | CCGGAUUUCGAUUUGGUUUGACU (SEQ ID NO: 2608) |
| bantam-5p_Mut Position 11 | CCGGUUUUCGCUUUGGUUUGACU (SEQ ID NO: 2613) |
| bantam-5p_Mut Position 14 | CCGGUUUUCGAUUAGGUUUGACU (SEQ ID NO: 2598) |

Figure 11 (Cont.)

| Bantam-3p | UGAGAUCAUU<u>UU</u>GAAAGCUGAUU (SEQ ID NO.: 2617) |
|---|---|
| U ➔ G | UGAGAUCAUUU<u>G</u>GAAAGCUGAUU (SEQ ID NO.: 2655) |
| U ➔ C | UGAGAUCAUUU<u>C</u>GAAAGCUGAUU (SEQ ID NO.: 2656) |
| U ➔ A | UGAGAUCAUUU<u>A</u>GAAAGCUGAUU (SEQ ID NO.: 2657) |

SIMPLE ONE-STEP REAL-TIME MOLECULAR SYSTEM FOR MICRORNA DETECTION

CROSS-REFERENCE TO RELATED APPLICATIONS

This patent application is a U.S. National Phase application under 35 U.S.C. § 371 of International Application No. PCT/SG2017/050086, filed on 24 Feb. 2017, entitled A SIMPLE ONE-STEP REAL-TIME MOLECULAR SYSTEM FOR MICRORNA DETECTION, which claims the benefit of priority of Singapore provisional application No. 10201601384T, filed on 24 Feb. 2016, the contents of which were incorporated by reference in their entirety for all purposes.

INCORPORATION BY REFERENCE

The content of the ASCII text file of the sequence listing named "9322P124_Updated_Sequence_Listing_ST25", which is 598 kb in size, was created on and electronically submitted via EFS-Web Dec. 28, 2020 is incorporated herein by reference in its entirety.

FIELD OF THE INVENTION

The present invention relates to molecular biology in particular molecular sensor. In particular, the present invention relates to a molecular sensor for the detection of a target nucleic acid sequence, specifically, a target miRNA.

BACKGROUND OF THE INVENTION

MicroRNAs (miRNAs) are short, non-coding RNAs that regulate many important biological processes in development, physiology and disease. miRNAs are often involved in regulatory feedback loops, where aberrations in cellular processes trigger miRNAs to act to restore target levels. Therefore, the ability to respond dynamically to changing conditions is inferred to be an essential function of miRNAs. miRNAs are also an emerging class of biomarkers, which are misregulated in cancer and neurodegenerative diseases. miRNA expression signatures have shown promise for use in prognosis and as predictors of clinical response. Therefore, tools for the detection and quantification of miRNAs have broad applicability.

Current methods to detect miRNAs include northern blotting, amplification-based methods such as real-time polymerase chain reaction (PCR), rolling circle amplification and isothermal amplification, deep sequencing, as well as hybridization-based techniques such as microarrays and in situ hybridization. These methods are suitable for the detection of purified RNA in vitro. To study miRNAs in vivo, quencher-fluorophore based systems such as molecular beacons have been used. These nucleic acid-based probes require additional delivery agents for efficient cellular uptake. For instance, polyethyleneimine-grafted graphene nanoribbons were used to deliver LNA-modified molecular beacon probes to detect miR-21 in HeLa cells. An alternative approach involves the use of genetically encoded sensor transgenes with miRNA target sites introduced into the 3' UTR of a GFP reporter. Down-regulation of the sensor therefore reports miRNA activity. This approach allows for good spatial resolution to visualize miRNA activity in vivo, but has limited capacity for temporal resolution of miRNA dynamics, due to the relatively slow turnover of the GFP reporter.

Thus, there is a need for the provision of improved molecular sensors, system and methods which can be used for the detection of miRNAs.

SUMMARY OF THE INVENTION

In the first aspect, the present invention refers to an isolated nucleic acid sequence for detecting the presence of a target nucleic acid sequence, wherein the isolated nucleic acid sequence is capable of forming bimolecular interactions with the target nucleic acid sequence, wherein the isolated nucleic acid sequence forms a ternary complex stabilizing a detection agent when binding the target nucleic acid sequence and wherein the isolated nucleic acid sequence comprises the following structure:

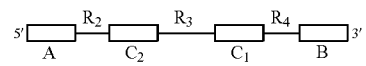

wherein A and B are domains forming stabilizing secondary structures, wherein $C_1$ and $C_2$ are domains that bind to the target nucleic acid sequence, wherein $R_2$ and $R_4$ are regions of nucleic acids that do not bind with the target nucleic acid sequence, and wherein $R_3$ is a region of nucleic acids capable of stabilising a detection agent upon the isolated nucleic acid binding to the target nucleic acid sequence.

In the second aspect, the present invention provides a method of detecting a target nucleic acid sequence in an animal, wherein the method comprises using the isolated nucleic acid sequence of the first aspect.

In the third aspect, the present invention provides a method of determining if a subject has a disease or is at increased risk of developing a disease, wherein said method comprises providing a sample comprising nucleic acids from a subject and detecting one or more target nucleic acid sequences that bind to the isolated nucleic acid of the first aspect.

In the fourth aspect, the present invention provides a method of treating a patient which has a disease or is at increased risk of developing a disease, wherein said method comprises (i) providing a sample comprising nucleic acids from a patient and detecting one or more target nucleic acid sequences that bind to the isolated nucleic acid sequence of the first aspect, and (ii) administering to the patient one or more therapeutic agents for the treatment of the disease associated with the one or more target nucleic acid sequences detected in (i).

In the fifth aspect, the present invention provides a kit comprising the isolated nucleic acid of the first aspect and a detection agent described herein.

BRIEF DESCRIPTION OF THE DRAWINGS

The invention will be better understood with reference to the detailed description when considered in conjunction with the non-limiting examples and the accompanying drawings, in which.

Figure 1:
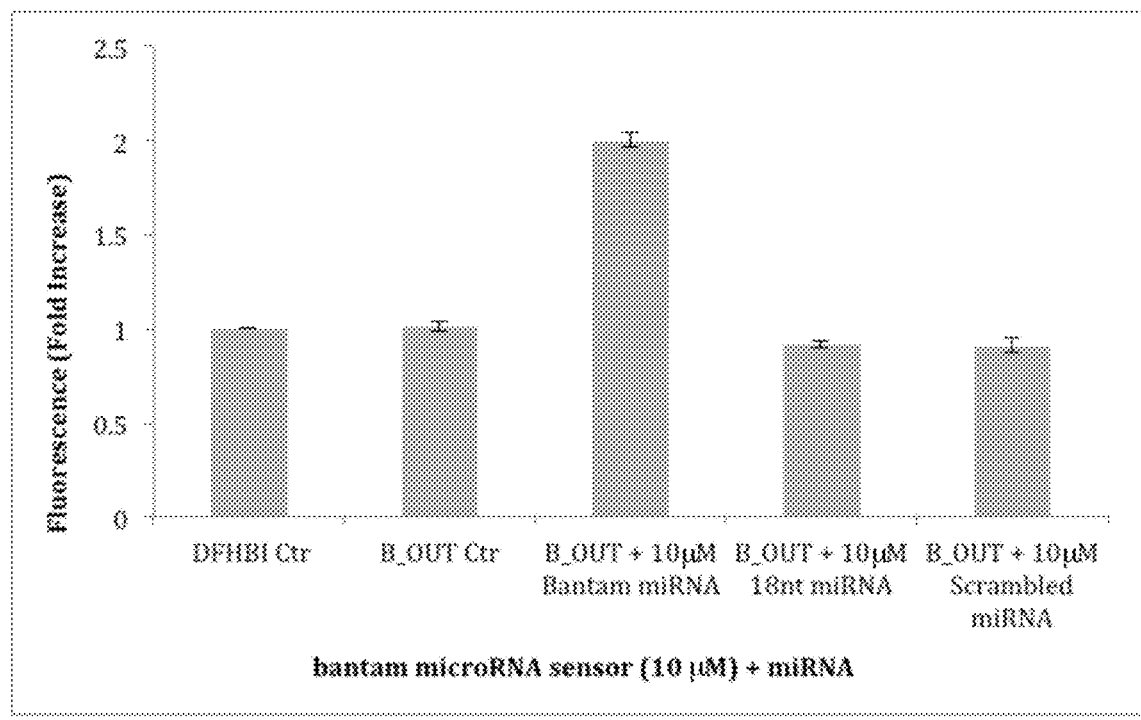
FIG. 1A shows a bar chart of the fluorescence levels of Pandan bantam miRNA sensor used with different miRNA samples. The sequences of the different miRNA samples are listed in FIG. 1B. The y-axis represents the fold increase in the fluorescence level as compared to the DFHBI control.

The bars represent, from left to right, the following experimental setups: DFHBI control (negative control); Pandan bantam miRNA sensor+DFHBI; Pandan bantam miRNA sensor+DFHBI+10 µM bantam miRNA; Pandan bantam miRNA sensor+DFHBI+10 µM of a random 18 nucleotides long miRNA; Pandan bantam miRNA sensor+DFHBI+ scrambled mRNA. The results demonstrate that a fold increase in the fluorescence level of the Pandan bantam miRNA sensor only occurs when the target bantam miRNA is present in the sample. The data presented in FIG. 1 is only illustrating that in the absence of the target miRNA, the sensor will not show any significant increase in fluorescence level. The sensor used in the experiments illustrated in FIG. 1 is an intermediate form of the sensor, that does not include the variable stem-loop P4. This sensor could be optimized to arrive at the final Pandan sensor design by incorporating the variable stem-loop P4, which shows a more significant fold increase in fluorescence levels, as shown in FIG. 2 (80 to 100 fold increase when the Pandan bantam sensor binds to 1 µM bantam miRNA).

Figure 2:
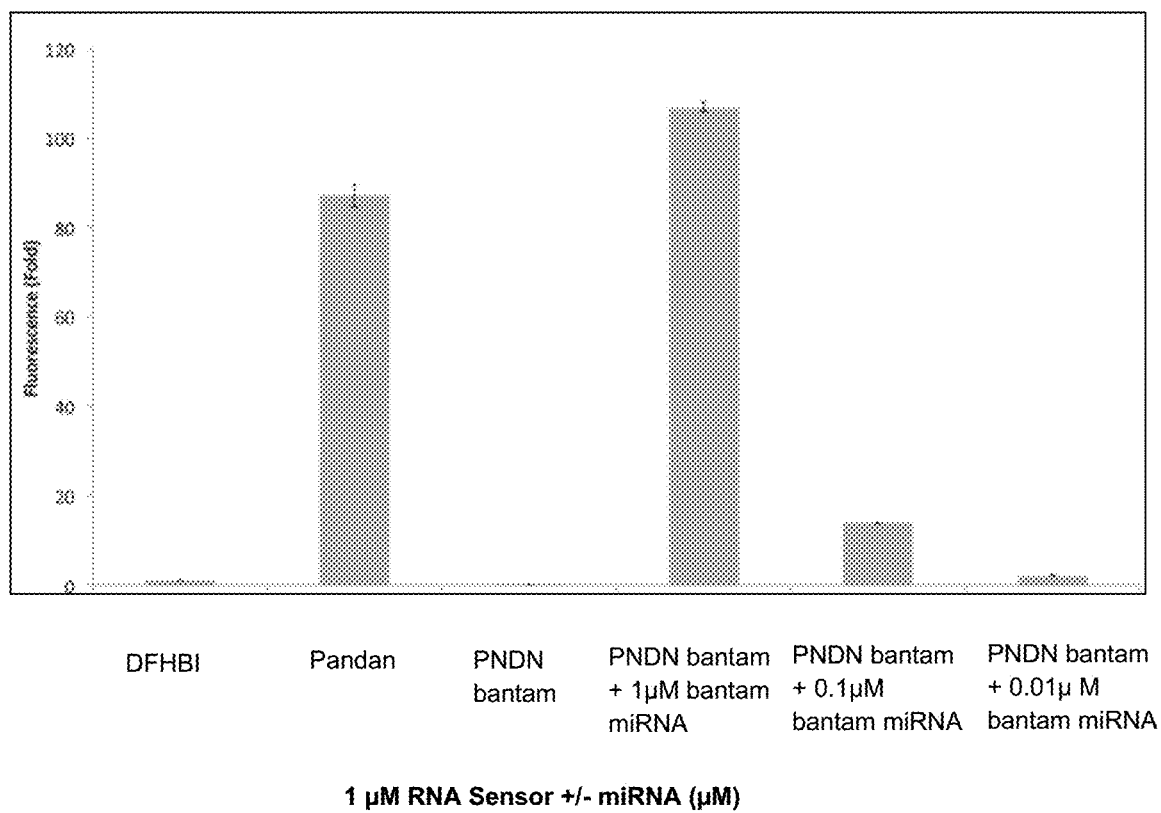

FIG. 2 shows a bar chart of the fluorescence levels of 1 µM Pandan bantam-5p miRNA sensor used with different miRNA samples. The y-axis represents the fold increase in the fluorescence level as compared to the DFHBI only control. The bars represent, from left to right, the following experimental setups: DFHBI alone (negative control); Pandan (positive control); Pandan bantam-5p miRNA sensor+ DFHBI; Pandan bantam-5p miRNA sensor+DFHBI+1 µM bantam-5p miRNA; Pandan bantam-5p miRNA sensor+ DFHBI+0.1 µM bantam-5p miRNA; Pandan bantam-5p miRNA sensor+DFHBI+0.01 µM bantam-5p miRNA. The positive control is a Pandan RNA molecule, with the bantam miRNA encoded with its cognate Pandan sensor as one continuous molecule. The sequence of the positive control thus consists of the Pandan sensor at the 5' end and the bantam miRNA at the 3'end. The results demonstrate that a significant fold increase in the fluorescence level of the Pandan bantam-5p miRNA sensor only occurs when the target bantam-5p miRNA is present in the sample, and the fold increase depends on the amount of target miRNA present in the sample.

FIG. 3A illustrates the structure of stem loop 3 (SL3) of an exemplary Pandan sensor, Pandan 263a, with (right panel) and without (left panel) an extension in the stem, and a bar chart of the fluorescence levels of 1 µM Pandan miR-263a sensor with or without an extension of the stem in SL3, used with different miRNA samples. The y-axis represents the fold increase in the fluorescence level as compared to the Pandan miR-263a sensor+DFHBI control. The pairs of bars represent, from left to right, the following experimental setups: Pandan miR-263a sensor alone; Pandan miR-263a sensor+DFHBI control (negative control); Pandan miR-263a sensor+DFHBI+1 µM miR-263a; Pandan miR-263a sensor+DFHBI+0.1 µM miR-263a; Pandan miR-263a sensor+DFHBI+0.01 µM miR-263a. The left bar in each pair represents the fluorescence level when the Pandan miR-263a sensor without the extension in SL3 is used, while the right bar in each pair represents the fluorescence level when the Pandan miR-263a sensor with the extension in SL3 is used. The results demonstrate that extending the stem loop in SL3 improves the strength of the Pandan sensor signal for the detection of miR-263a.

FIG. 3B illustrates the structure of stem loop 3 (SL3) of another exemplary Pandan sensor, Pandan bantam, with (right panel) and without (left panel) an extension in the stem, and a bar chart of the fluorescence levels of 1 µM Pandan bantam miRNA sensor with or without an extension of the stem in SL3, used with different miRNA samples. The y-axis represents the fold increase in the fluorescence level as compared to the Pandan bantam miRNA sensor+DFHBI control. The pairs of bars represent, from left to right, the following experimental setups: Pandan bantam sensor+ DFHBI control (negative control); Pandan bantam sensor+ DFHBI+1 µM bantam miRNA; Pandan bantam sensor+ DFHBI+0.1 µM bantam miRNA; Pandan bantam sensor+ DFHBI+0.01 µM bantam miRNA. The left bar in each pair represents the fluorescence level when the Pandan bantam miRNA sensor without the extension in SL3 is used, while the right bar in each pair represents the fluorescence level when the Pandan bantam miRNA sensor with the extension in SL3 is used. The results demonstrate that extending the stem loop in SL3 improves the strength of the Pandan sensor signal for the detection of bantam miRNA.

FIG. 3C illustrates the structure of stem loop 3 (SL3) of another exemplary Pandan sensor, Pandan miR1000, with (right panel) and without (left panel) an extension in the stem, and a bar chart of the fluorescence levels of 1 µM Pandan miR1000 sensor with or without an extension of the stem in SL3, used with different miRNA samples. The y-axis represents the fold increase in the fluorescence level as compared to the Pandan miR-1000 sensor+DFHBI control. The pairs of bars represent, from left to right, the following experimental setups: Pandan miR-1000 sensor alone; Pandan miR-1000 sensor+DFHBI control (negative control); Pandan miR-1000 sensor+DFHBI+104 miR-1000; Pandan miR-1000 sensor+DFHBI+0.1 µM miR-1000; Pandan miR-1000 sensor+DFHBI+0.01 µM miR-1000. The left bar in each pair represents the fluorescence level when the Pandan miR-1000 sensor without the extension in SL3 is used, while the right bar in each pair represents the fluorescence level when the Pandan miR-1000 sensor with the extension in SL3 is used. The results demonstrate that extending the stem loop in SL3 improves the strength of the Pandan sensor signal for the detection of miR1000.

FIG. 3D shows a bar chart of the fluorescence levels of 1 µM Pandan sensor with different extension lengths of the stem in SL3, used with 1 µM of different miRNA samples. The y-axis represents the fold increase in the fluorescence level as compared to the respective Pandan sensor without any extension in SL3 used with the same miRNA sample. The groups of bars represent, from left to right, the following experimental setups: Pandan miR-1000 sensor+104 miR-1000; Pandan miR-263a sensor+1 µM miR-263a; Pandan bantam-5p sensor+1 µM bantam-5p. The left bar in each group represents the fluorescence level when the Pandan sensor used has an extended 6 nucleotides-long stem in SL3. The middle bar in each group represents the fluorescence level when the Pandan sensor used has an extended 9 nucleotides-long stem in SL3. The right bar in each group represents the fluorescence level when the Pandan sensor used has an extended 12 nucleotides-long stem in SL3. The results demonstrate that further extensions of the stem in SL3 beyond 6 nucleotides long do not further improve the Pandan sensor signal.

FIG. 3E shows a bar chart of the fluorescence levels of 1 µM Pandan sensor with different extension lengths of the stem in stem loop 4 (SL4), used with 1 µM of bantam-3p miRNA. The y-axis represents the fold increase in the fluorescence level as compared to the respective Pandan sensor without any extension in SL4. The groups of bars represent, from left to right, the following experimental setups: Pandan bantam-3p sensor+DFHBI only (negative control); Pandan bantam-3p sensor+DFHBI+1 µM bantam-3p miRNA. The left bar in each group represents the fluorescence level when the Pandan sensor used has an extended 7 nucleotides-long stem in SL4. The middle bar in each group represents the fluorescence level when the Pandan sensor used has an extended 10 nucleotides-long stem in SL4. The right bar in each group represents the fluorescence level when the Pandan sensor used has an extended 13 nucleotides-long stem in SL4. The results demonstrate that extending the stem loop in SL4 does not improve the strength of the Pandan sensor signal.

FIG. 3F shows a bar chart of the fluorescence levels of 1 μM of different Pandan sensor with extension length of 6 nucleotides in the stem of SL3, used with 1 μM of different miRNA samples. The y-axis represents the fold increase in the fluorescence level as compared to the respective Pandan sensor with DFHBI (negative control). The groups of bars represent, from left to right, the following experimental setups: Pandan sensor+DFHBI; Pandan sensor+DFHBI+1 μM dme miRNA. The first bar in each group represents the fluorescence level when a Pandan sensor targeting dme miRNA124 is used. The second bar in each group represents the fluorescence level when a Pandan sensor targeting dme miRNA14 is used. The third bar in each group represents the fluorescence level when a Pandan sensor targeting dme miRNA1 is used. The fourth bar in each group represents the fluorescence level when a Pandan sensor targeting dme miRNA184 is used. The fifth bar in each group represents the fluorescence level when a Pandan sensor targeting dme miRNA252 is used. The results demonstrate that extending the stem loop in SL3 improves the strength of the Pandan sensor signal for the detection of *drosophila* miRNAs.

Figure 4:
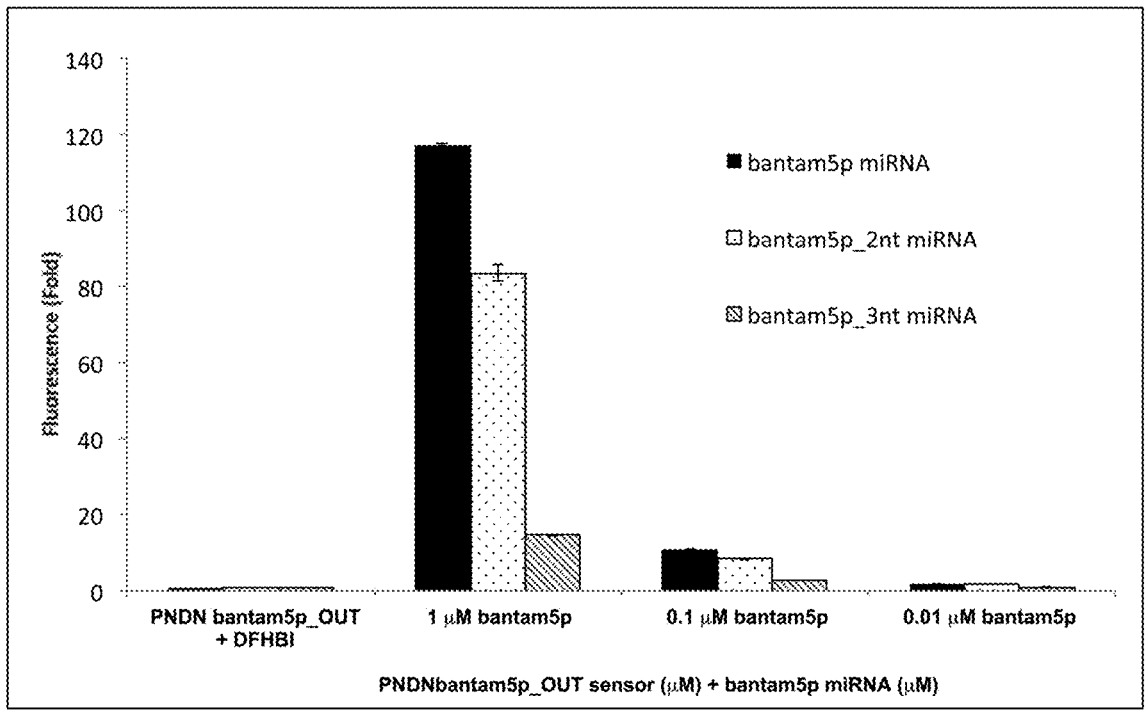

FIG. 4A shows a bar chart of the fluorescence levels of 1 μM Pandan bantam-5p miRNA sensor used with different miRNA samples. The y-axis represents the fold increase in the fluorescence level as compared to the Pandan bantam-5p miRNA sensor+DFHBI control. The groups of bars represent, from left to right, the following experimental setups: Pandan bantam-5p miRNA sensor+DFHBI control (negative control); Pandan bantam-5p miRNA sensor+DFHBI+1 μM bantam-5p miRNA; Pandan bantam-5p miRNA sensor+DFHBI+0.104 bantam-5p miRNA; Pandan bantam-5p miRNA sensor+DFHBI+0.01 μM bantam-5p miRNA. The left bar in each group represents the fluorescence level when the synthesized target bantam-5p miRNA is used. The middle bar in each group represents the fluorescence level when the bantam-5p miRNA with two nucleotides mutation is used. The right bar in each group represents the fluorescence level when the bantam-5p miRNA with three nucleotides mutation is used. The results demonstrate that the Pandan bantam-5p miRNA sensor can strongly differentiate between the target bantam-5p miRNA and the bantam-5p miRNA with mutations. The sequences of the bantam-5p miRNA with and without mutations are listed in FIG. 4B.

FIG. 5A shows a bar chart of the fluorescence levels of 1 μM Pandan snoR442 sensor used with RNA samples with different amount of snoR442 small RNAs. The y-axis represents the fold increase in the fluorescence level as compared to the Pandan snoR442 sensor+DFHBI control. The groups of bars represent, from left to right, the following experimental setups: Pandan snoR442 sensor+DFHBI control (negative control); Pandan snoR442 sensor+DFHBI+1 μM snoR442 small RNA; Pandan snoR442 sensor+DFHBI+0.1 μM snoR442 small RNA; Pandan snoR442 sensor+DFHBI+0.01 μM snoR442 small RNA. The left bar in each group represents the fluorescence level when a Pandan sensor targeting part 1 of snoR442 small RNA is used. The middle bar in each group represents the fluorescence level when a Pandan sensor targeting part 2 of snoR442 small RNA is used. The right bar in each group represents the fluorescence level when both Pandan sensors targeting part 1 and part 2 of snoR442 small RNA are used in equal amount. The results demonstrate that Pandan sensors designed against each half of the snoR442 miRNA can be used to detect full length snoR442, and that these two Pandan sensors can be used in combination to increase the overall signal derived from the same amount of the target snoR442 miRNA. The sequences of full length snoR442 miRNA as well as the first and second half of the snoR442 miRNA are listed in FIG. 5B.

Figure 6:
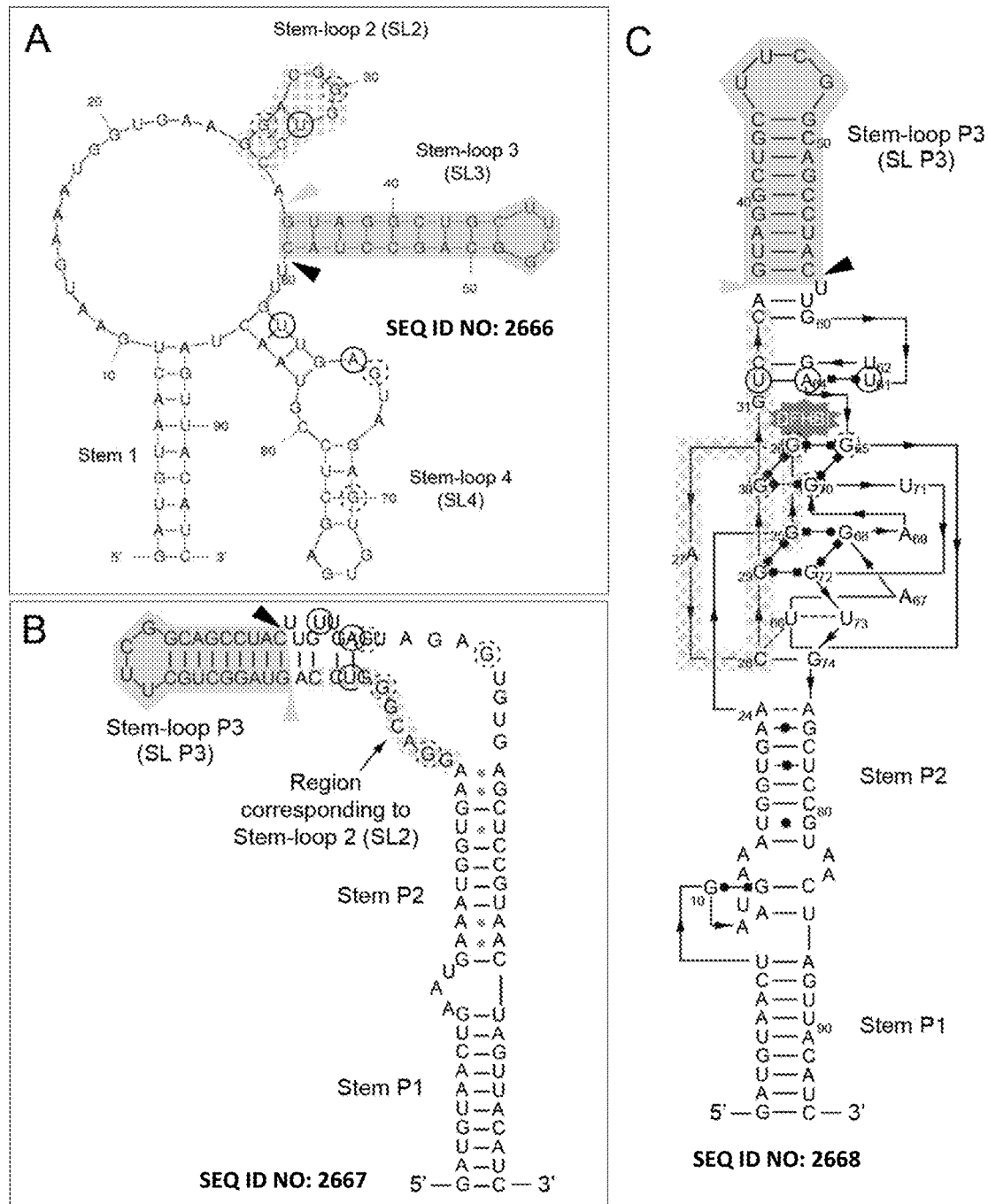

FIG. 6 illustrates Pandan structure and sensor design strategy. FIG. 6A represents the computationally (mFold) predicted structure of the Spinach sensor. FIG. 6B is a simplified 2D representation of the solved crystal structure of Spinach2 sensor. FIG. 6C is a detailed 2D representation of the solved crystal structure of Spinach2 sensor. As the helices were differently named in the two solved structures, for consistency, the paired regions are named P1, P2 and P3. Dashed circled Gs form the top tetrad of the core G-quadruplex region and solid circles highlight the bases in the base triple that is required for Spinach folding. Solid grey shading highlight the bases in each structure that correspond to Stem-loop P3, and checkered grey shading highlight the bases in each structure that correspond to Stem-loop 2 of the predicted structure in FIG. 6A. The grey arrowhead in each structure indicates the position where SL P3 5' was inserted, and the black arrowhead indicates the position where SL P3 3' was inserted (See FIG. 7). Adding another stem loop (stem-loop P4, as shown in FIG. 8) to Spinach2 allows the new molecule to function as a sequence-specific sensor.

Figure 7:
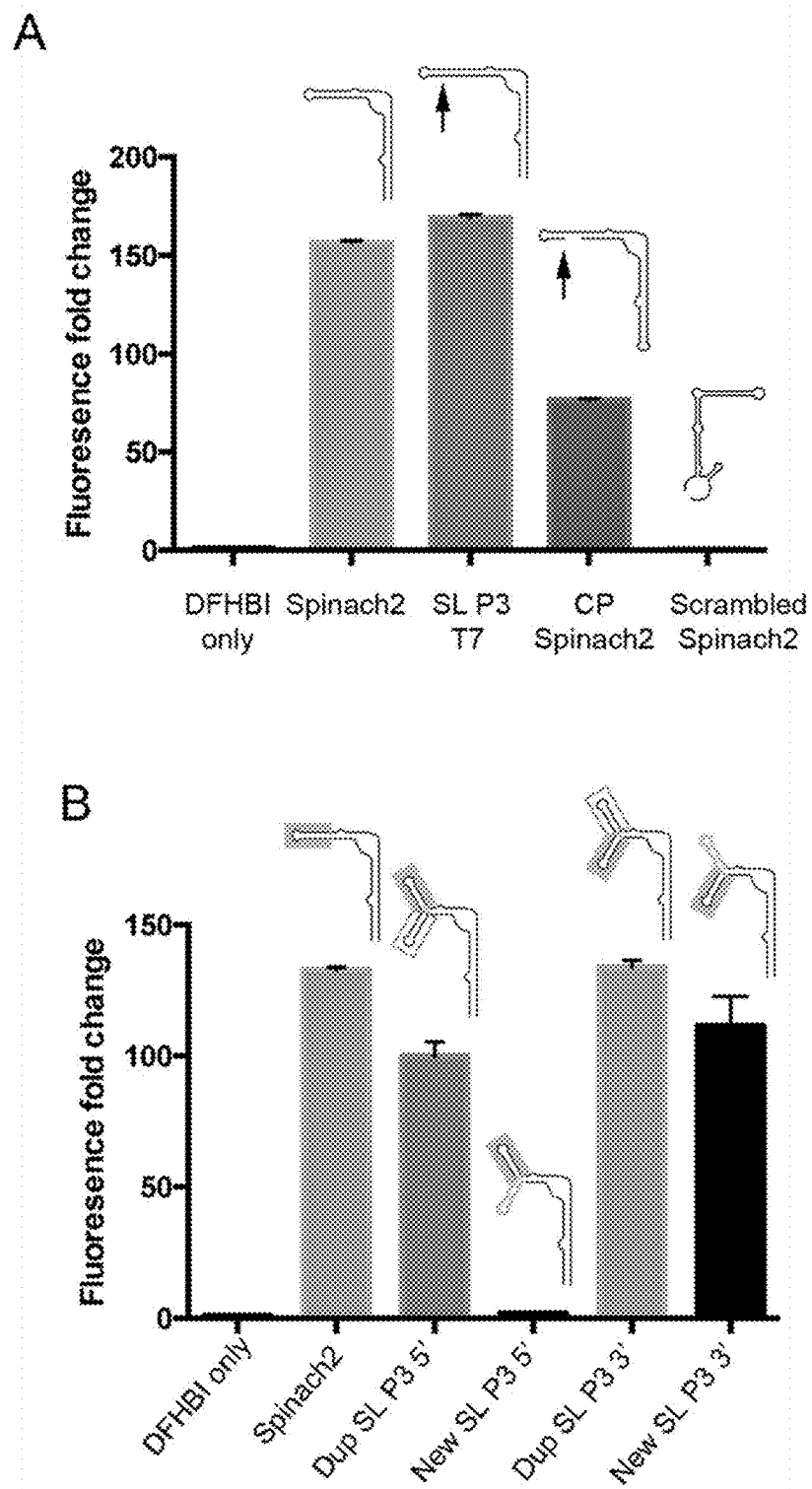

FIG. 7 illustrates features of the Pandan sensor design. FIG. 7A shows fluorescence intensity fold change of DFHBI+Spinach2 and modified versions of Spinach2 compared to the DHFBI-only control. All samples contained DFHBI. Schematic structures of the different RNAs are shown. Arrows indicate the position of the inserted partial T7 transcriptional start site, GGGA. FIG. 7B shows fluorescence intensity fold change of sensor designs testing the addition of extra adjacent stem-loop sequences 5' and 3' of SL P3 (positions indicated in arrowheads in FIG. 6A to C. Dup SL P3 indicates insertion of a second copy of the SL P3 stem-loop. New SL indicates insertion of an independent randomly chosen sequence of the same length. All samples contained DFHBI.

Figure 8:
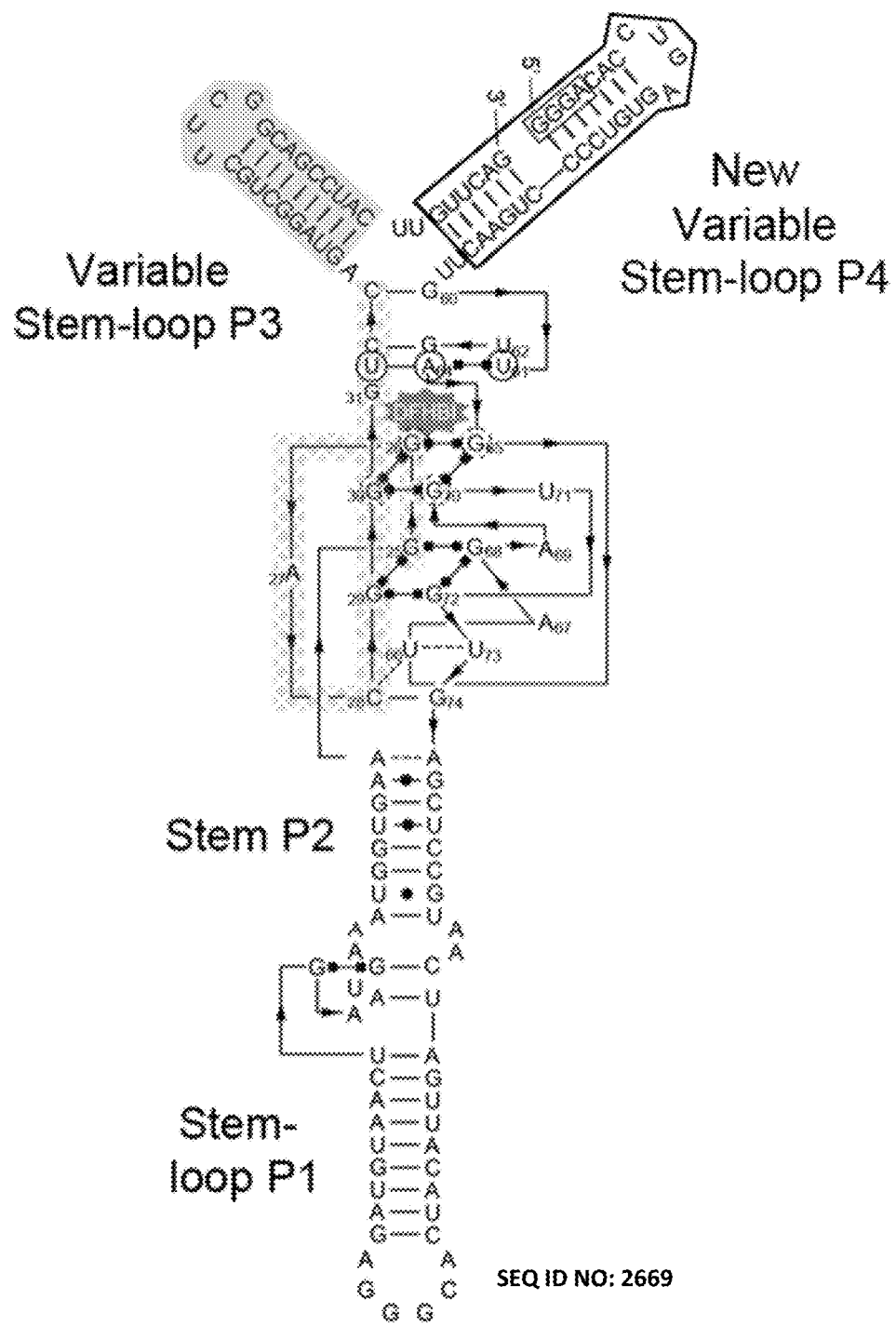

FIG. 8 is a diagram showing the single-molecule version of Pandan with the 5' and 3' ends in the added stem-loop P4. The addition of the new stemloop P4 allows it to act as a sensor for the detection of the target RNA. Shading is consistent with FIG. 6A to C. The GGGA partial transcriptional start site is boxed. SL P3: Stem-loop P3; SL P3 T7: Spinach2 with an additional GGGA partial T7 transcriptional start site in SLP3; CP Spinach2: circularly permuted (CP) Spinach2. Fluorescence intensity fold change shown is with respect to DFHBI-only controls. Cartoons used in FIGS. 7A and 7B are based on the simplified 2D structure as shown in FIG. 6B.

Figure 9:
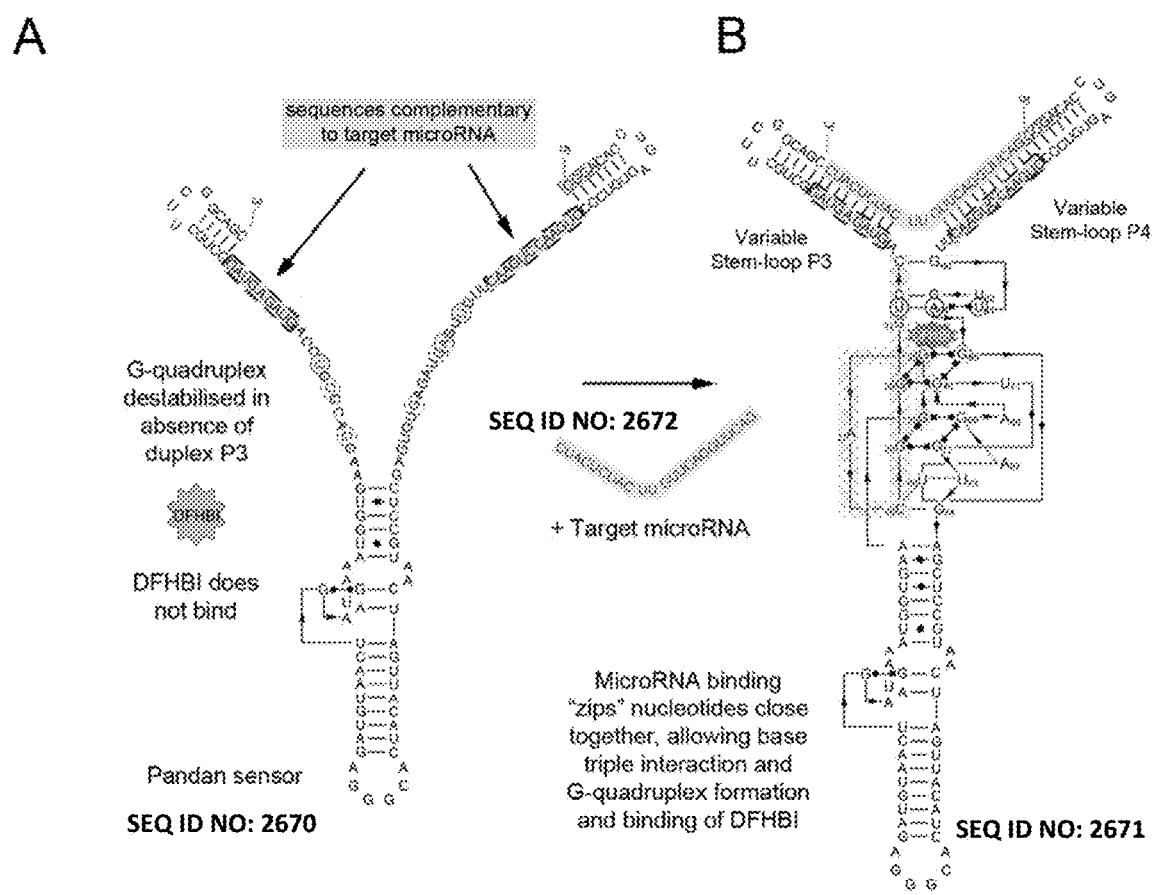

FIG. 9 demonstrates that Pandan is a bimolecular miRNA sensor. FIG. 9A illustrates that absence of the target miRNA prevents duplexes P3 and P4 from forming, hence destabilizing the G-quadruplex and base triplet required for proper folding and binding of DFHBI. FIG. 9B shows that pairing between miRNA and sensor backbone in stem-loops P3 and P4 allows for stable complex folding with DFHBI. The arrow indicates the second unpaired Uracil (U) 3' of SL P3, 5' of SL P4. The GGGA partial transcriptional start site is boxed. Shading is consistent with FIGS. 6A to C. The target miRNA is shaded in solid grey. Sequences complementary to the target miRNA are in dashed boxes.

Figure 10:
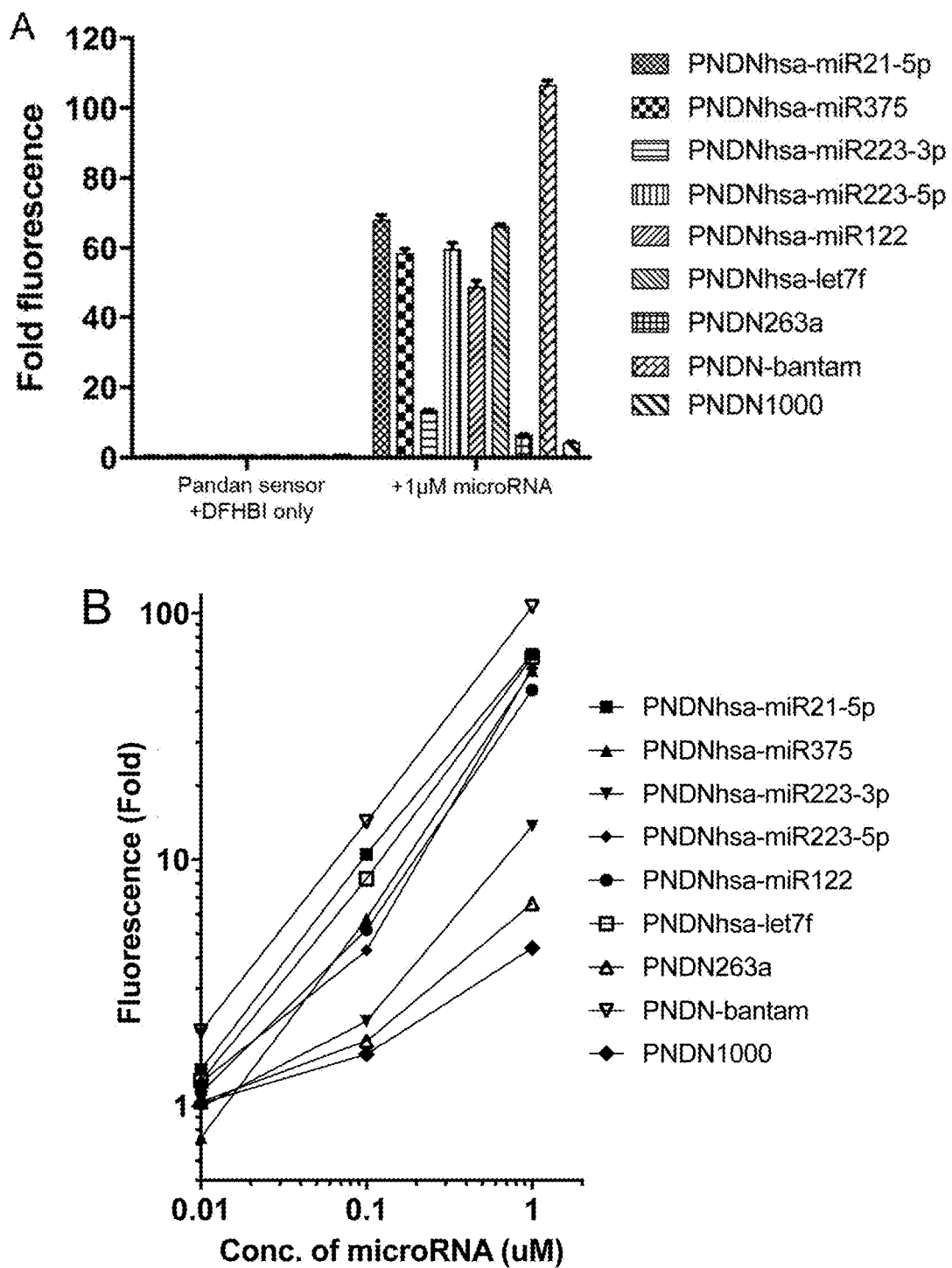

FIG. 10 illustrates sequence-specific miRNA detection by Pandan sensors. FIG. 10A shows fluorescence intensity fold change of Pandan sensors for several different miRNAs compared to each respective sensor+DFHBI alone. FIG. 10B shows fluorescence intensity fold change of Pandan sensors as a function of miRNA concentration for miRNAs from FIG. 10A. All samples contained DFHBI. FIG. 10C shows fluorescence intensity fold change of 1 μM bantam-5p Pandan sensor in the absence or presence of 1 μM bantam-5p miRNA, compared to that of 1 μM Spinach2, 1 μM CP Spinach2 and 1 μM Pandan bantam-5p-IN (where the sequence of bantam-5p miRNA is encoded into Pandan as one continuous molecule). Fluorescence intensity fold change shown is with respect to DFHBI-only controls. All samples contained DFHBI.

Figure 11:
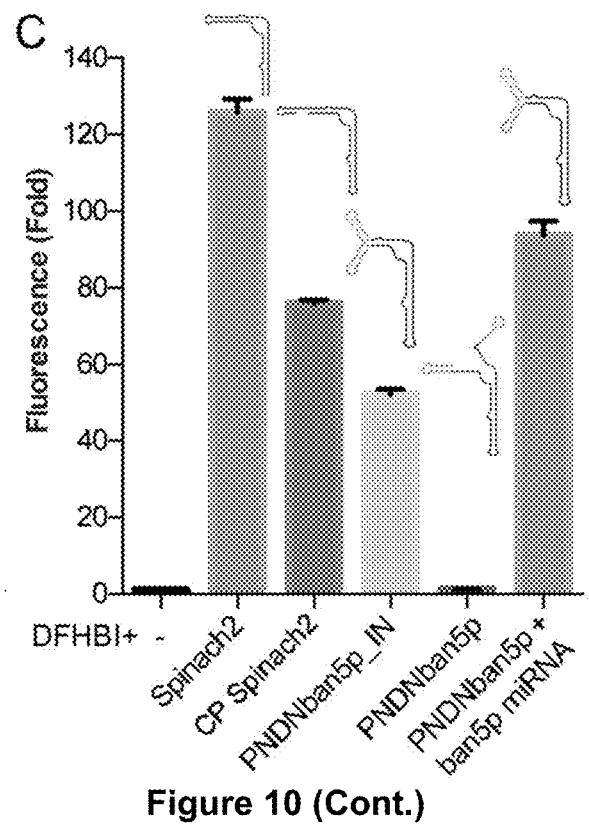
Figure 11:
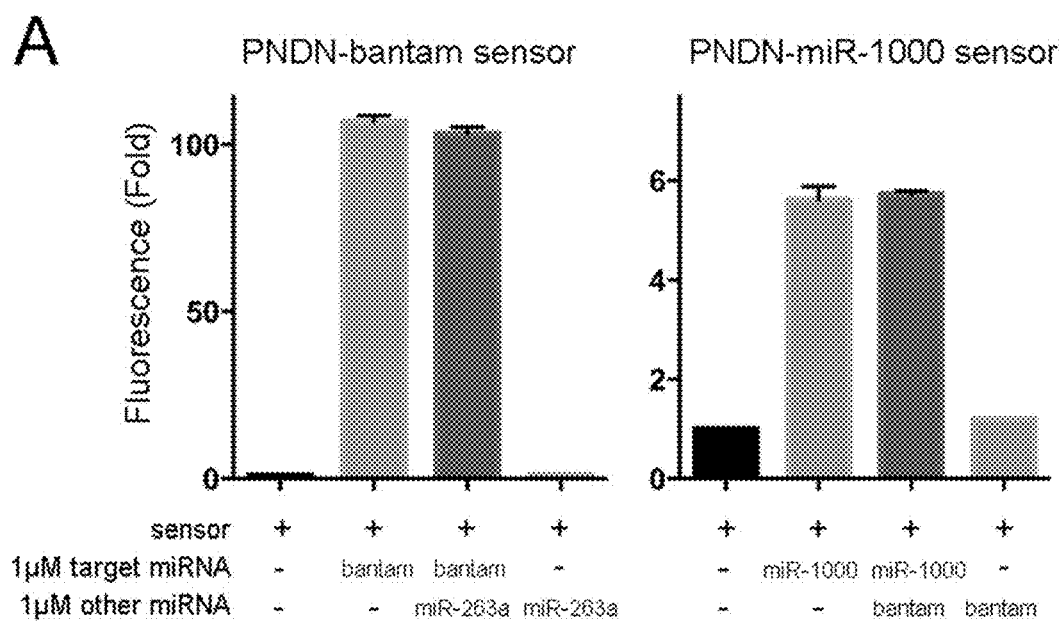
Figure 11:
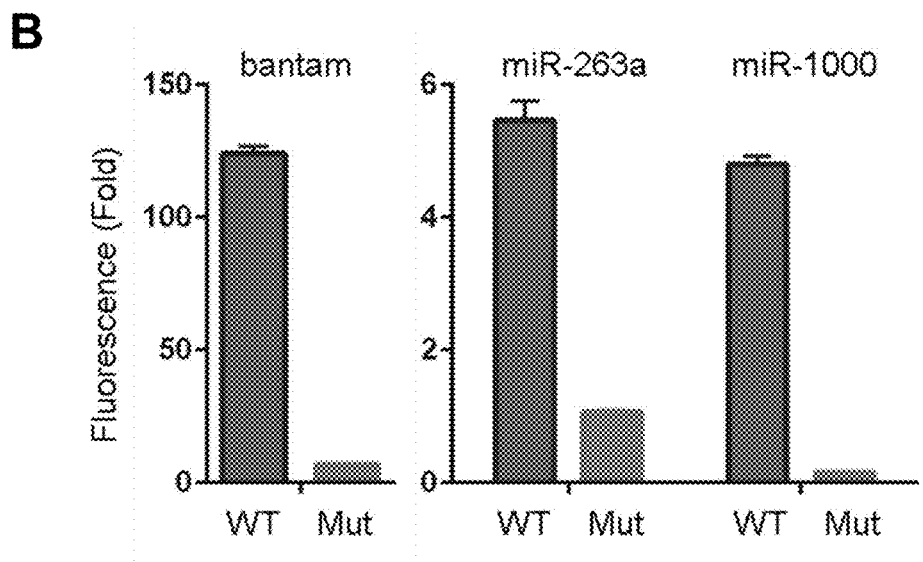
Figure 11:
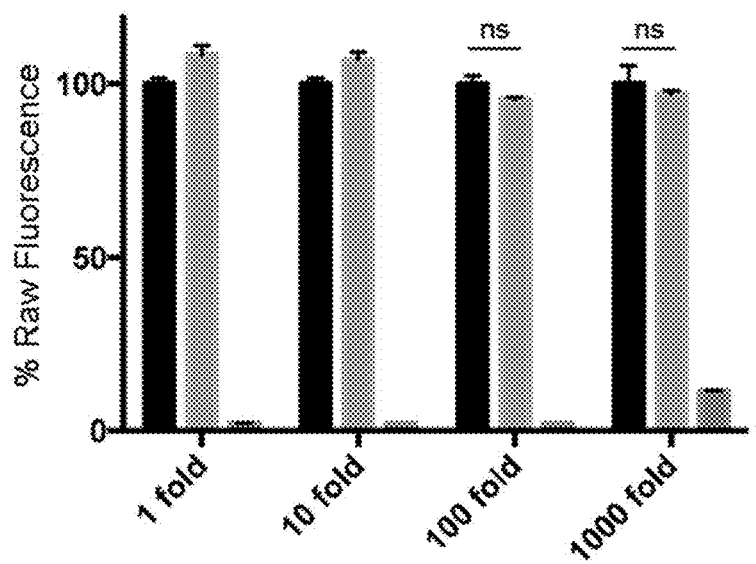

FIG. 11 demonstrates the parameters affecting the selectivity of Pandan sensors. FIG. 11A shows fluorescence intensity fold change of Pandan sensors for bantam-5p and miR-1000 miRNAs tested with target and non-target miRNAs. FIGS. 11B and 11C show fluorescence intensity of Pandan sensors for bantam-5p, miR-263a and miR-1000 miRNAs tested with perfectly complementarity and sequence modified miRNAs. FIG. 11B shows the effect of mutating three residues in the miRNA 5' end. FIG. 11C shows the effects of single residue mutations at different positions in the miRNA. Sequence changes are underlined. FIG. 11D shows the performance of the bantam-3p Pandan sensor with increasing fold excess of competing *Drosophila* total RNA, expressed as a percentage of raw fluorescence of sensor with bantam-3p in the absence of competing RNA. The presence of up to 1000-fold of competing RNA did not decrease the ability of bantam-3p sensor to detect bantam-3p ($P>0.05$). Fluorescence intensity fold change shown is with respect to sensor+DFHBI-only controls (negative control without miRNA). All samples contained DFHBI.

Figure 12:
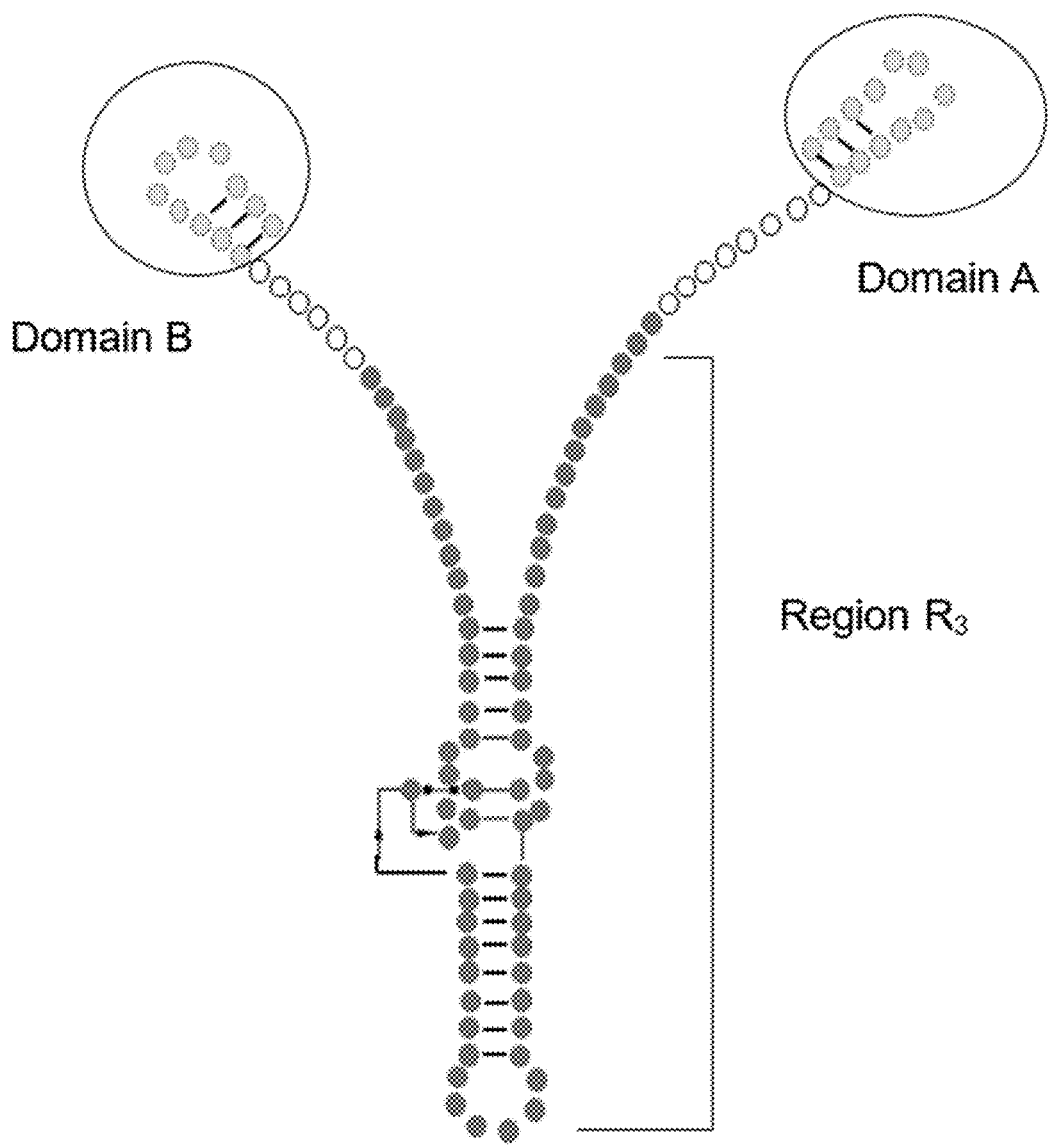

FIG. 12 shows a schematic representation of the structure of a Pandan aptamer before the target nucleic acid sequence is bound. Region R3 represents the core structure (solid circles represent the nucleotides in R3), $C_1$ and $C_2$ represent the variable domains which complementarily bind to the 5' and 3' ends of the target nucleic acid sequence (circles represent the nucleotides in $C_1$ and $C_2$). Domains A and B represent the variable domains that could form stabilizing secondary structures (dashed circles represent the nucleotides in Domains A and B). The schematic representation is an illustration of the structure only, the number of circles in each region and domain does not necessarily represent the exact number of nucleotides in each region and domain.

Figure 13:
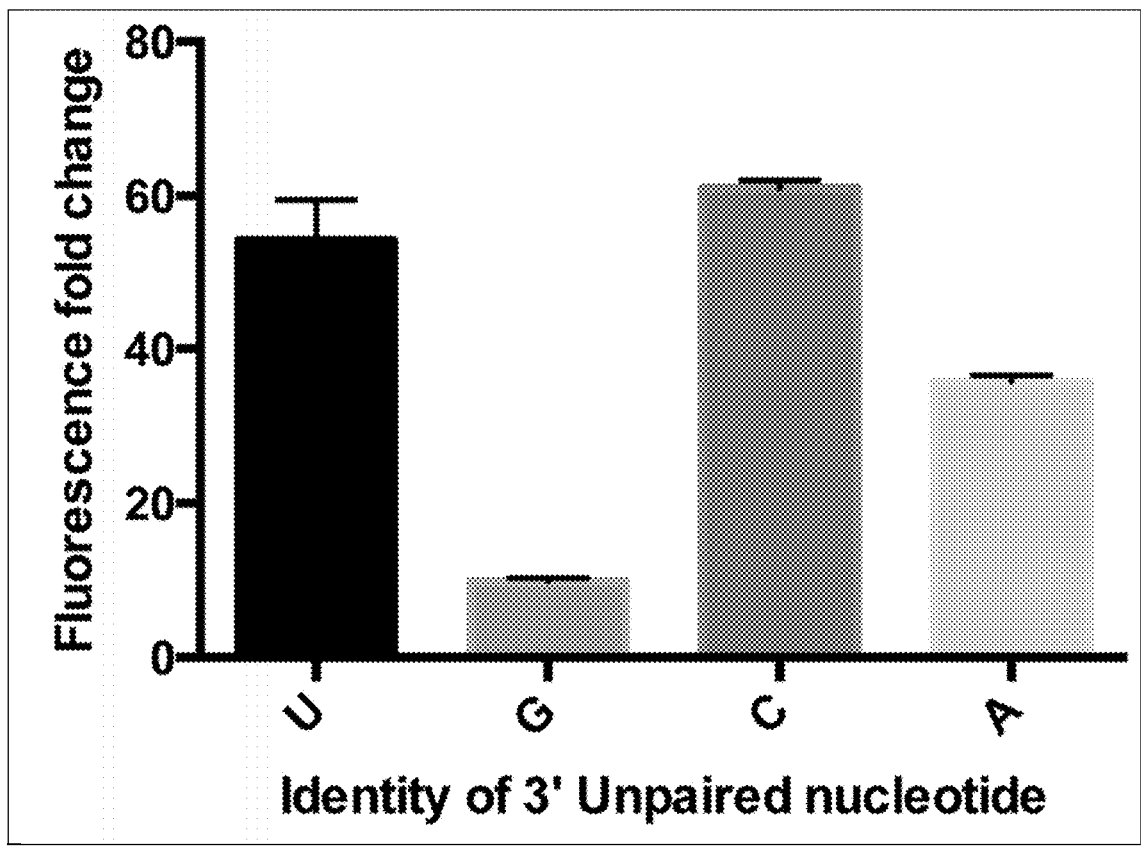

FIG. 13 shows a bar chart of the fluorescence levels of Pandan bantam-3p sensor used with bantam-3p target miRNAs with different nucleotides in the middle unbound region of the target miRNA. The y-axis represents the fold increase in the fluorescence level as compared to the Pandan bantam-3p sensor+DFHBI control. The bars represent, from left to right, the following experimental setups: Pandan bantam-3p sensor+DFHBI+bantam-3p miRNA without mutation; Pandan bantam-3p sensor+DFHBI+bantam-3p miRNA with U to G mutation; Pandan bantam-3p sensor+DFHBI+bantam-3p miRNA with U to C mutation; Pandan bantam-3p sensor+DFHBI+bantam-3p miRNA with U to A mutation. The nucleotide sequences of the target miRNAs are presented in the table in FIG. 13. The two unpaired nucleotides in each target miRNA are underlined, and the sequence change of the 3' unpaired nucleotide is in bold. Binding with target miRNA having a cytosine (C) at the second unbound nucleotide position gives the Pandan sensor the highest fluorescence fold increase over the negative control (above 60 folds), following by uracil (U) (about 55 folds), followed by adenine (about 35 folds). Binding with target miRNA having a guanine (G) at the second unbound nucleotide position gives the Pandan sensor the lowest fluorescence fold increase over the negative control (about 10 folds). The results demonstrate that the sensor can function regardless of the identity of the second unbound nucleotide in the unbound region of the target miRNA. (Comment: FIG. 13 shows that fluorescence is even better when the nucleotide is a C and pretty good when it is an A. Even when it is a G, there is still 10 fold fluorescence change. However, this one example is not sufficient to extrapolate as it could be context dependent. It merely shows that that nucleotide is not restricted to a Uracil (even though all the sensors we designed have a Uracil is that position as you can see from the sequences we provided).

DETAILED DESCRIPTION OF THE PRESENT INVENTION

The present invention provides a simple one-step molecular system for the detection of miRNA.

In a first aspect, the present invention refers to an isolated nucleic acid sequence for detecting the presence of a target nucleic acid sequence, wherein the isolated nucleic acid sequence is capable of forming bimolecular interactions with the target nucleic acid sequence, wherein the isolated nucleic acid sequence forms a ternary complex stabilising a detection agent when binding the target nucleic acid sequence and wherein the isolated nucleic acid sequence comprises the following structure:

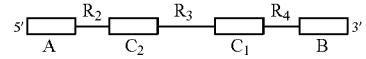

wherein A and B are domains forming stabilizing secondary structures, wherein $C_1$ and $C_2$ are domains that bind to the target nucleic acid sequence, wherein $R_2$ and $R_4$ are regions of nucleic acids that do not bind with the target nucleic acid sequence, and wherein $R_3$ is a region of nucleic acids capable of stabilising a detection agent upon the isolated nucleic acid binding to the target nucleic acid sequence.

The structure of the isolated nucleic acid sequence of the first aspect can further comprise regions $R_1$ and $R_5$, wherein $R_1$ is upstream from domain A and $R_5$ is downstream from domain B, and wherein $R_1$ and $R_5$ are regions of nucleic acids that do not bind with the target nucleic acid sequence and are capable of forming secondary structures.

The term "nucleic acid sequence" as used herein refers to a polymeric form of nucleotides. It may be in the form of RNA or single-stranded DNA, that comprise purine and pyrimidine bases, or other natural, chemically or biochemically modified, non-natural, or derivative nucleotide bases. References to single stranded nucleic acids include references to the sense or antisense strands. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. These analogs are those molecules having some structural features in common with a naturally occurring nucleoside or nucleotide such that when incorporated into a nucleic acid or oligonucleotide sequence, they allow hybridization with a naturally occurring nucleic acid sequence. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "complementary" as used herein refers to a nucleotide or nucleotide sequence that hybridizes to a given nucleotide or nucleotide sequence. For instance, for RNA, the nucleotide A is complementary to the nucleotide U, and vice versa, and the nucleotide C is complementary to the nucleotide G, and vice versa. Complementary nucleotides include those that undergo Watson and Crick base pairing and those that base pair in alternative modes.

The term "isolated" as used herein means altered "by the hand of man" from its natural state, i.e., if it occurs in nature, it has been changed or removed from its original environment, or both. Thus, the term "isolated nucleic acid sequence" as used herein refers to a nucleic acid sequence which has been purified from the sequences which flank it in a naturally occurring state. It can also be used to refer to a synthesized nucleic acid sequence which does not exist in nature. In some examples, the term "isolated nucleic acid sequence" and "synthesized nucleic acid sequence" can be used interchangeably.

The term "target nucleic acid sequence" as used herein refers to the nucleic acid sequence of interest that is to be detected using the molecular sensor system of the present invention. The molecular sensor system includes the molecular sensor which is the isolated nucleic acid sequence of the first aspect. The target nucleic acid sequence can be a single-stranded nucleic acid sequence or double-stranded nucleic acid sequence. Preferably, it is a single-stranded nucleic acid sequence. The nucleic acid sequence can be a deoxyribonucleic acid (DNA) sequence or a ribonucleic acid (RNA) sequence. Preferably, it is an RNA sequence. Examples of RNA sequences include but are not limited to, microRNA (miRNA), short interfering RNA (siRNA), small RNA (sRNA), messenger RNA (mRNA), non-coding RNA (ncRNA), transfer RNA (tRNA), ribosomal RNA (rRNA), transfer-messenger RNA (tmRNA), clustered regularly interspaced short palindromic repeats RNA (CRIPSR RNA), antisense RNA, pre-mRNA and pre-miRNA. In one specific example, the RNA sequence is a miRNA sequence.

The term "microRNA" (abbreviated miRNA) as used herein refers to a small non-coding RNA molecule. It generally functions in RNA silencing and post-transcription regulation of gene expression. While the majority of miRNAs are located within the cell, some miRNAs, commonly known as circulating miRNAs or extracellular miRNAs, have also been found in extracellular environment, including various biological fluids and cell culture media. In some examples, the length of the miRNAs can be between 10 to 12, or between 12 to 14, or between 14 to 16, or between 16 to 18, or between 18 to 20, or between 20 to 22, or between 22 to 24, or between 24 to 26, or between 26 to 28, or between 28 to 30, or 11, 13, 15, 17, 19, 21, 23, 25, 27, or 29 nucleotides long.

The terms "domain" and "region" as used herein refer to different sections of the linear nucleic acid sequence of the isolated nucleic acid sequence of the first aspect. Domain refers to sections that either have direct interaction with the target nucleic acid sequence or the detection agent. Regions, on the other hand, are sections of the linear nucleic acid sequence that are not known to directly interact with either the target nucleic acid sequence or the detection agent before the target nucleic acid sequence is bound. However, regions can be capable of stabilising a detection agent upon the isolated nucleic acid of the first aspect binding to the target nucleic acid sequence.

The term "secondary structure" of a nucleic acid molecule refers to the base-pairing interactions within a single molecule or set of interactive molecules, and can be represented as a list of bases which are paired in a nucleic acid molecule. The secondary structures of biological DNAs and RNAs tend to be different: biological DNA mostly exists as fully base-paired double helices, while biological RNA is single stranded and often forms complicated base-pairing interactions due to its increased ability to form hydrogen bonds stemming from the extra hydroxyl group in the ribose sugar. Examples for secondary structures of nucleic acids include, but are not limited to, single-nucleotide bulges, three-nucleotide bulges, stems, stem loops, t-RNA type structures, cloverleaves, tetraloops, pseudoknots, symmetrical internal loops, asymmetrical internal loops, three stem junctions, four stem junctions, two-stem junctions or coaxial stacks or combinations thereof. Specific examples of secondary structures include stems, stem loops, t-RNA type structures, cloverleaves, tetraloops, pseudoknots or combinations thereof.

As used herein, the term "stem loop", also known as a "hairpin loop", refers to a secondary nucleic acid structure that forms when two regions of the same strand, usually complementary in nucleotide sequence when read in opposite directions, base-pair to form a double helix that ends with an unpaired loop.

The term "ternary complex" as used herein refers to a complex containing three different molecules that are bound together. These three different molecules can be the isolated nucleic acid sequence of the first aspect, the target nucleic acid sequence that binds to the isolated nucleic acid sequence of the first, and the detection agent.

In some examples, domains A and B form stem loops. The lengths of the stems of the stem loops of domains A and B are independent from each other, and can be the same or different. For example, each of the stems of the stem loops of domains A and B can be between 1 to 5, or between 5 to 10, or between 10 to 15, or between 15 to 20, or 3, 4, 5, 6, 7, 8, 9, 10 nucleotides long. In some specific examples, each of the stems of the stem loops of domains A and B is 5 or 6 or 7 nucleotides long. In some specific examples, the stem of the stem loop of domain B is 6 nucleotides long.

In some examples, when the length of the stem of the stem loop of domain B increases from 3 nucleotides long to 4 nucleotides long, or from 4 nucleotides long to 5 nucleotides long, or from 5 nucleotides long to 6 nucleotides long, the signal strength of the sensor upon binding the target nucleic acid sequence will increase. In some examples, the signal strength is increased by 0.5 fold, 1 fold, 1.5 folds, 2 folds, 2.5 folds or 3 folds, or between 0.2 fold to 5 folds.

In some examples, the nucleotides of domains $C_1$ and $C_2$ complementarily bind to the opposite ends of the target nucleic acid sequence respectively. For example, domain $C_1$ can complementarily bind to the 5' end of the target nucleic acid sequence, while domain $C_2$ can complementarily bind to the 3' end of the target nucleic acid sequence, and vice versa. The complementary binding can be either partially complementary or fully complementary. For example, domain $C_1$ can be between about 70 to about 80%, or between about 80% to about 90%, or between about 90% to about 100%, or between about 75% to about 85%, or between about 85% to about 95%, or between about 95% to about 100%, or between about 88% to about 98%, or about 90%, about 91%, about 92%, about 93%, about 94%, about 95%, about 96%, about 97%, about 98%, about 99% or about 100% complementary to the 5' end of the target nucleic acid sequence; and domain $C_2$ can be between about 70 to about 80%, or between about 80% to about 90%, or between about 90% to about 100%, or between about 75% to about 85%, or between about 85% to about 95%, or between about 95% to about 100%, or between about 88% to about 98%, or about 90%, about 91%, about 92%, about 93%, about 94%, about 95%, about 96%, about 97%, about 98%, about 99% or about 100% complementary to the 3' end of the same target nucleic acid sequence, and vice versa. The lengths of domains $C_1$ and $C_2$ are independent from each other, and can be the same or different. For example, each of domains $C_1$ and $C_2$ can be between 3 to 5, or between 5 to 10, or between 10 to 15, or between 15 to 20, or between 20 to 30, or between 30 to 40, or between 40 to 50, or 3, 4, 5, 6, 7, 8, 9, 10 nucleotides long. In some specific examples, domain $C_1$ is 6 nucleotides long. In some other examples, domain $C_2$ is 8 nucleotides long.

In some examples, domain A can form a stem-loop. In some other examples, domain $C_2$ and the 3' end of the target nucleic acid sequence can complementarily bind to each other to form a stem. In some examples, (i) the stem-loop formed by domain A and (ii) the stem formed between domain $C_2$ and the 3' end of the target nucleic acid sequence together form a stem-loop. In some examples, this stem-loop formed by (i) and (ii) above is called stem-loop P4. The nucleic acid sequence of stem-loop P4 is variable, depending on the sequence of the target nucleic acid, and consequently the sequence of domain $C_2$. In some examples, all the isolated nucleic acid sequences of the first aspect comprise stem-loop P4.

In some examples, the target nucleic acid sequence to be detected does not fully bind to the isolated nucleic acid of the first aspect. A middle region of nucleic acids may be present between the 5' and the 3' ends of the target nucleic acid sequence, and the middle region does not bind to either domain $C_1$ or $C_2$. In some examples, the middle region can be between 1 to 2, or between 2 to 4, or between 4 to 6, or between 6 to 8, or between 8 to 10, or between 10 to 12, or between 12 to 14, or between 14 to 16, or between 16 to 18, or between 18 to 20, or 3, 5, 7, 9, 11, 13, 15, 17 or 19 nucleotides in length. In one specific example, the middle region is 2 nucleotides in length. In one specific example, the middle region comprises one uracil nucleotide. In some examples, the middle region comprises one uracil nucleotide and one nucleotide selected from: uracil, adenine, guanine and cytosine. In one specific example, the middle region comprises two uracil nucleotides. In one specific example, the middle region consists of two uracil nucleotides. In some other examples, the middle region does not comprise any uracil nucleotides.

In some examples, regions $R_2$ and/or $R_4$ are capable of forming secondary or linear structures. $R_2$ or $R_4$ can be between 0 to 20, or between 1 to 5, or between 5 to 10, or between 10 to 15, or between 15 to 20, or between 4 to 7, or between 8 to 15, or between 15 to 20 nucleotides in length. In some examples, $R_2$ or $R_4$ is absent. In some examples, both $R_2$ and $R_4$ are absent. When $R_2$ is absent, domain A is directly linked to domain $C_2$. When $R_4$ is absent, domain B is directly linked to domain $C_1$. Preferably, the regions $R_2$ and $R_4$ do not interfere with interactions of the domains of the isolated nucleic acid sequence of the first aspect.

In some examples, region $R_1$ or $R_5$ is between 0 to 20, or between 1 to 5, or between 5 to 10, or between 10 to 15, or between 15 to 20, or between 4 to 7, or between 8 to 15, or between 15 to 20 nucleotides in length. Preferably, the regions $R_1$ and $R_5$ do not interfere with interactions of the domains of the isolated nucleic acid sequence of the first aspect.

In some examples, the region $R_3$ is between 0 to 100, or between 1 to 5, or between 5 to 10, or between 10 to 15, or between 15 to 20, or between 20 to 30, or between 30 to 40, or between 40 to 50, or between 50 to 60, or between 60 to 70, or between 70 to 80, or between 80 to 90, or between 90 to 100 nucleotides in length.

Preferably, the target nucleic acid sequence is competitively bound to the isolated nucleic acid sequence of the first aspect.

In some examples, region $R_3$ can further comprise defined domains and regions. In some examples, the isolated nucleic acid sequence of the first aspect can also have the following structure:

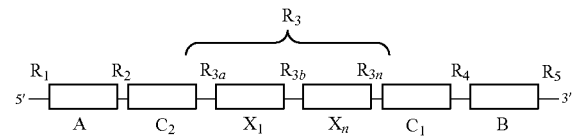

wherein $X_1$ to $X_n$ are domains containing nucleic acids that interact with the detection agent in a ternary complex and wherein $X_n$ denotes a variable number of domains, and wherein $R_1$ to $R_5$ are as previously defined and wherein $R_{3a}$ and $R_{3b}$ to $R_{3n}$ are the regions between the domains $C_2$ and $X_1$, $X_1$ to $X_n$, and $X_n$ and $C_1$ respectively, wherein $R_{3n}$ denotes a variable number of regions according to the number of $X_n$ domains present.

In some examples, the total number of domains $X_n$ can be 2, 3, 4, 5, 6, 7, 8, 9 or 10. The maximum number of domains $N_n$ present in the isolated nucleic acid sequence is the total number of nucleotides within the domains $X_n$ that interact with the detection agent in a ternary complex. In some examples, each of domains $X_1$ to $X_n$ is between 1 to 5, or between 5 to 10, or between 10 to 15, or between 15 to 20, or between 4 to 7, or between 8 to 15, or between 10 to 18, or 6, 7, 9, 10, 11, 12, 13, 14, 15, 16, 17, 18, 19, 20, 21, 22, 23, 24, 25 nucleotides in length. The length of each of domains $X_1$ to $X_n$ is independent, and can be the same or different from each other.

Region $R_3$ is capable of stabilising a detection agent once the isolated nucleic acid sequence of the first aspect binds to the target nucleic acid sequence.

The term "detection agent" as used herein refers to a substance that is capable of producing a detectable signal once being activated. A detection agent can be a chemical compound or a macromolecule, and it can be activated upon sensing its target analyte. Examples of such detection agents include but are not limited to fluorophore, chromophore, photophore, pigment and chromatophore.

The term "fluorophore" as used herein refers to a fluorescent chemical compound that can re-emit light upon light excitation. Fluorophores typically contain several combined aromatic groups, or planar or cyclic molecules with several π bonds. Although sometimes being used alone, fluorophores are more generally covalently bonded to a macromolecule. Examples of fluorophore include but are not limited to 4-(3,4,5-trimethoxybenzylidene)-1,2-dimethylimidazol-5-one ("TMBI"); 4-(4-hydroxy-3,5-dimethoxy-benzylidene)-1,2-dimethyl-imidazol-5-one ("DMHBI"); difluoro-4-hydroxybenzylidene)-1,2-dimethyl-imidazol-5-one ("DFHBI"); (E)-4-(3,5-difluoro-4-hydroxybenzylidene)-1-methyl-5-oxo-4,5-dihydro-1H-imidazole-2-carbaldehyde O-methyl oxime ("DFHBI-methyloxime"); 4-(3,5-dichloro-4-hydroxybenzylidene)-1,2-dimethyl-imidazol-5-one; 4-(3,5-dibromo-4-hydroxybenzylidene)-1,2-dimethyl-imidazol-5-one; 4-(2-hydroxybenzylidene)-1,2-dimethyl-imidazol-5-one ("o-HBI"); 4-(2-methoxybenzylidene)-1,2-dimethyl-imidazol-5-one; 4-(3-fluoro-4-hydroxy-5-methoxybenzylidene)-1,2-dimethyl-imidazol-5-one; 4-(4-(dimethylamino)benzylidene)-1,2-dimethyl-imidazol-5-one ("DMABI"); 4-(4-(t-butylthio)benzylidene)-1,2-dimethyl-imidazol-5-one; 4-(4-(methylthio)benzylidene)-1,2-dimethyl-imidazol-5-one; 4-(4-cyanobenzylidene)-1,2-dimethyl-imidazol-5-one; 4-(3,5-difluoro-4-acetate)benzylidene-1,2-dimethyl-imidazol-5-one; 4-(4-hydroxy-3-nitrobenzylidene)-1,2-dimethyl-imidazol-5-one; 4-(4-hydr oxy-3-methoxy-5-nitrobenzylidene)-1,2-dimethyl-imidazol-5-one; 4-(4-methoxy-3-nitrobenzylidene)-1,2-dimethyl-imidazol-5-one; 4-(4-bromobenzylidene)-1,2-dimethyl-imidazol-5-one; 4-(4-chlorobenzylidene)-1,2-dimethyl-imidazol-5-one; 4-(4-hydroxybenzylidene)-1,2-dimethyl-imidazol-5-one ("p-HBI"); 4-((indol-7-yl)methylene)-1,2-dimethyl-imidazole-5-one; 4-((indol-3-yl)methylene)-1,2-dimethyl-imidazol-5-one; 4-((indol-3-yl)methylene)-1-methyl-2-phenyl-imidazole-5-one; 4-(4-hydroxy-3,5-dimethoxybenzylidene)-1-methyl-2-phenyl-imidazole-5-one; 4-(4-(dimethylamino)benzylidene)-1-methyl-2-phenyl-imidazole-5-one; 4-(4-hydroxybenzydene)-2-acetyl-1-methyl-imidazole-5-one; 4-(4-hydroxybenzylidene)-1-methyl-2-prop-1-enyl-imidazole-5-one; 3-(4-(4-hydroxybenzylidene)-4,5-dihydro-1-methyl-5-oxo-imidazol-2-yl)acrylamide; 3-(4-(4-hydroxybenzylidene)-4,5-dihydro-1-methyl-5-oxo-imidazol-2-yl)acrylic acid; methyl 3-(4-(4-hydroxybenzylidene)-4,5-dihydro-1-methyl-5-oxo-imidazol-2-yl)acrylate; 4-(3,5-difluoro-4-hydroxybenzylidene)-1-methyl-2-((E)-2-nitro vinyl)-1H-imidazol-5(4H)-one ("DFAN"); 4-(3-fluoro-4-hydroxy-5-methoxybenzylidene)-1-methyl-2-((E)-2-nitro vinyl)-1H-imidazol-5(4H)-one; 4-(3-fluoro-4-hydroxy-5-methoxybenzylidene)-1-methyl-5-oxo-4,5-dihydro imidazole-2-carbaldehyde O-methyl oxime; 4-(3-fluoro-4-hydroxy-5-methoxybenzylidene)-1-methyl-5-oxo-4,5-dihydroimidazole-2-carbaldehyde oxime ("MFHO"); 4-(3,5-difluoro-4-hydroxybenzylidene)-1-methyl-5-oxo-4,5-dihydro-1H-imidazole-2-carbaldehyde oxime; 4-(3,5-difluoro-4-hydroxybenzydene)-1-methyl-5-oxo-4,5-dihydro-1H-imidazole-2-carb oxylic acid; 4-(3-fluoro-4-hydroxy-5-methoxybenzydene)-1-methyl-5-oxo-4,5-dihydro imidazole-2-carboxylic acid; 4-(3,5-difluoro-4-hydroxybenzylidene)-1-methyl-5-oxo-4,5-dihydro-1H-imidazole-2-carboxamide; difluoro-4-hydroxybenzylidene)-N,1-dimethyl-5-oxo-4,5-dihydroimidazole-2-carboxamide; 4-(3-fluoro-4-hydr oxy-5-methoxybenzydene)-N,1-dimethyl-5-oxo-4,5-dihydro imidazole-2-carboxamide; methyl 3-((Z)-4-(3,5-difluoro-4-hydroxybenzylidene)-1-methyl-5-oxo-4,5-dihydro-1H-imidazol-2-yl)acrylate ("DFAME"); methyl 3-(4-(3-fluoro-4-hydroxy-5-methoxybenzylidene)-1-methyl-5-oxo-4,5-dihydro-1H-imidazol-2-yl)acrylate, 4-(3-fluoro-4-hydroxy-5-methoxybenzylidene)-1,2-dimethyl-1H-imidazol-5(4H)-one ("MFHBI"), and combinations thereof. In one specific example, the fluorophore is DFHBI.

The isolated nucleic acid sequence of the first aspect can be a ribonucleic acid (RNA) sequence, a deoxyribonucleic acid (DNA) sequence, a sequence comprising non-natural nucleic acids, or a sequence comprising nucleic acid analogues. In one specific example, the isolated nucleic acid sequence of the first aspect is an RNA sequence.

In some examples, the isolated nucleic acid sequence of the first aspect comprises the sequence as defined by SEQ ID NO: 2, or by a combination comprising SEQ ID NO: 1, followed by SEQ ID NO: 2658, followed by SEQ ID NO: 2659. In some examples, the sequence as defined by SEQ ID NO:2 represents the core template of the isolated nucleic acid sequence of the first aspect. In one example, the core template refers to the sequence of the nucleotides in region $R_3$, as illustrated in FIG. 12.

In some examples, the isolated nucleic acid sequence of the first aspect comprises any one of the sensor sequences as listed in Table 1, i.e. nucleic acid sequences of SEQ ID NOs: 2618 to 2632, 2634, 2636, 2638, 2640, 2641, 2643, 2645, 2647, 2649, 2651, 2652 and 2654.

TABLE 1

Examples of RNA sensors.

| SEQ ID NO. of sensor | Name of Sensor | Sequence of Sensor (5' to 3') | Name of Target RNA | Sequence of Target RNA (5' to 3') |
|---|---|---|---|---|
| 2618 | PNDN-bantam-3p | GGGACACCUGAGUGUCCCAAUCAGCUUUCUUGUUGAGUAGAGUGUGA GCUCCGUAACUAGUUACAUCACGGGAGAUGUAACUGAAUGAAAUGGU GAAGGACGGGUCCAAAUGAUCUCAUGCUUCGGCA | bantam-3p | UGAGAUCAUUUU GAAAGCUGAUU (SEQ ID NO.: 2617) |
| 2619 | PNDN-dme-miR-263a | GGGACACCUGAGUGUCCCCCGUGAAUUCUUCCUUGUUGAGUAGAGU GUGAGCUCCGUAACUAGUUACAUCACGGGAGAUGUAACUGAAUGAAA UGGUGAAGGACGGGUCCAUGCCAUUUGCUUCGGCA | mir-263a | AAUGGCACUGGA AGAAUUCACGGG (SEQ ID NO.: 2609) |
| 2620 | PNDN-dme-miR-263a_6nt (PNDN-dme-miR-263a with 6nt in SL3) | GGGACACCUGAGUGUCCCCCGUGAAUUCUUCCUUGUUGAGUAGAGU GUGAGCUCCGUAACUAGUUACAUCACGGGAGAUGUAACUGAAUGAAA UGGUGAAGGACGGGUCCAUGCCAUUGGCUGCUUCGGCAGCC | | |
| 2621 | PNDN 263a_9nt (PNDN 263a with 9nt in SL3) | GGGACACCUGAGUGUCCCCCGUGAAUUCUUCCUUGUUGAGUAGAGU GUGAGCUCCGUAACUAGUUACAUCACGGGAGAUGUAACUGAAUGAAA UGGUGAAGGACGGGUCCAUGCCAUUGUAGGCUGCUUCGGCAGCCUAC | | |

TABLE 1-continued

Examples of RNA sensors.

| SEQ ID NO. of sensor | Name of Sensor | Sequence of Sensor (5' to 3') | Name of Target RNA | Sequence of Target RNA (5' to 3') |
|---|---|---|---|---|
| 2622 | PNDN 263a_12nt (PNDN 263a with 12nt in SL3) | GGGACACCUGAGUGUCCCCCGUGAAUUCUUCCUUGUUGAGUAGAGU GUGAGCUCCGUAACUAGUUACAUCACGGGAGUAGUAACUGAAUGAAA UGGUGAAGGACGGGUCCAUGCCAUUGACGUAGGCUGCUUCGGCAGCC UACGUC | | |
| 2623 | PNDN-dme-bantam5p | GGGACACCUGAGUGUCCCAGUCAAACCAUUGUUGAGUAGAGUGUGAG CUCCGUAACUAGUUACAUCACGGGAGAUGUAACUGAAUGAAAUGGUG AAGGACGGGUCCAUCGAAAACCGGUGCUUCGGCA | bantam5p | CCGGUUUUCGAU UUGGUUUGACU (SEQ ID NO.: 2599) |
| 2624 | PNDN-bantam-5p_6nt (PNDN-bantam-5p with 6nt in SL3) | GGGACACCUGAGUGUCCCAGUCAAACCAUUGUUGAGUAGAGUGUGAG CUCCGUAACUAGUUACAUCACGGGAGAUGUAACUGAAUGAAAUGGUG AAGGACGGGUCCAUCGAAAACCGGGGCUGCUUCGGCAGCC | | |
| 2625 | PNDN bantam5p_9nt (PNDN bantam5p with 9nt in SL3) | GGGACACCUGAGUGUCCCAGUCAAACCAUUGUUGAGUAGAGUGUGAG CUCCGUAACUAGUUACAUCACGGGAGAUGUAACUGAAUGAAAUGGUG AAGGACGGGUCCAUCGAAAACCGGGUAGGCUGCUUCGGCAGCCUAC | | |
| 2626 | PNDN bantam5p_12nt (PNDN bantam5p with 12nt SL3) | GGGACACCUGAGUGUCCCAGUCAAACCAUUGUUGAGUAGAGUGUGAG CUCCGUAACUAGUUACAUCACGGGAGAUGUAACUGAAUGAAAUGGUG AAGGACGGGUCCAUCGAAAACCGGGACGUAGGCUGCUUCGGCAGCCU ACGUC | | |
| 2627 | PNDN bantam5p_10nt (PNDN bantam5p with 10nt in SL4) | GGGACACUUGCUGACAAGUGUCCCAGUCAAACCAUUGUUGAGUAGAG UGUGAGCUCCGUAACUAGUUACAUCACGGGAGAUGUAACUGAAUGAA AUGGUGAAGGACGGGUCCAUCGAAAACCGGGGCUGCUUCGGCAGCC | | |
| 2628 | PNDN bantam5p_13nt (PNDN bantam5p 13nt in SL4) | GGGACACUUGCAGCUGACUGCAAGUGUCCCAGUCAAACCAUUGUUGA GUAGAGUGUGAGCUCCGUAACUAGUUACAUCACGGGAGAUGUAACUG AAUGAAAUGGUGAAGGACGGGUCCAUCGAAAACCGGGGCUGCUUCGG CAGCC | | |
| 2629 | PNDN-dme-miR-1000 | GGGACACCUGAGUGUCCCACUGCUGUGUUGUUGAGUAGAGUGUGAGC UCCGUAACUAGUUACAUCACGGGAGAUGUAACUGAAUGAAAUGGUGA AGGACGGGUCCAAGGACAAUAUUGCUUCGGCA | mir-1000 | AUAUUGUCCUGU CACAGCAGU (SEQ ID NO.: 2611) |
| 2630 | PNDN-dme-miR-1000_6nt (PNDN-dme-miR-1000 with 6nt in SL3) | GGGACACCUGAGUGUCCCACUGCUGUGUUGUUGAGUAGAGUGUGAGC UCCGUAACUAGUUACAUCACGGGAGAUGUAACUGAAUGAAAUGGUGA AGGACGGGUCCAAGGACAAUAUGGCUGCUUCGGCAGCC | | |
| 2631 | PNDN 1000_9nt (PNDN 1000 with 9nt in SL3) | GGGACACCUGAGUGUCCCACUGCUGUGUUGUUGAGUAGAGUGUGAGC UCCGUAACUAGUUACAUCACGGGAGAUGUAACUGAAUGAAAUGGUGA AGGACGGGUCCAAGGACAAUAUGUAGGCUGCUUCGGCAGCCUAC | | |
| 2632 | PNDN 1000_12nt (PNDN 1000 with 12nt in SL3) | GGGACACCUGAGUGUCCCACUGCUGUGUUGUUGAGUAGAGUGUGAGC UCCGUAACUAGUUACAUCACGGGAGAUGUAACUGAAUGAAAUGGUGA AGGACGGGUCCAAGGACAAUAUGACGUAGGCUGCUUCGGCAGCCUAC GUC | | |
| 2634 | PNDN-hsa-miR21-5p | GGGACACCUGAGUGUCCCGUCAACAUCUUGUUGAGUAGAGUGUGAGC UCCGUAACUAGUUACAUCACGGGAGAUGUAACUGAAUGAAAUGGUGA AGGACGGGUCCAUCGAUAAGCUACUGCUUCGGCA | hsa_miR-21-5p | GUAGCUUAUCAG ACUGAUGUUGAC (SEQ ID NO.: 2633) |
| 2636 | PNDN-hsa_miR-375 | GGGACACCUGAGUGUCCCCACGCGAGCCGUUGUUGAGUAGAGUGUGA GCUCCGUAACUAGUUACAUCACGGGAGAUGUAACUGAAUGAAAUGGU GAAGGACGGGUCCACGAACAAAUGCUUCGGCA | hsa_miR-375 | UUUGUUCGUUCG GCUCGCGUG (SEQ ID NO.: 2635) |

TABLE 1-continued

Examples of RNA sensors.

| SEQ ID NO. of sensor | Name of Sensor | Sequence of Sensor (5' to 3') | Name of Target RNA | Sequence of Target RNA (5' to 3') |
|---|---|---|---|---|
| 2638 | PNDN-hsa-miR-223-3p | GGGACACCUGAGUGUCCCUUGGGGUAUUUGUUGUUGAGUAGAGUGUGAGCUCCGUAACUAGUUACAUCACGGGAGAUGUAACUGAAUGAAAUGGUGAAGGACGGGUCCAAAACUGACUGCUUCGGCA | has_miR-223-3p | GUCAGUUUGUCAAAUACCCCAA (SEQ ID NO.: 2637) |
| 2640 | PNDN-hsa_miR-223-5p | GGGACACCUGAGUGUCCCCAACUCAGCUUGUCUUGUUGAGUAGAGUGUGAGCUCCGUAACUAGUUACAUCACGGGAGAUGUAACUGAAUGAAAUGGUGAAGGACGGGUCCAAUACACGUGCUUCGGCA | hsa_miR-223-5p | CGUGUAUUUGACAAGCUGAGUUG (SEQ ID NO.: 2639) |
| 2641 | PNDN-hsa_miR-122 | GGGACACCUGAGUGUCCCCAAACACCUUGUUGAGUAGAGUGUGAGCUCCGUAACUAGUUACAUCACGGGAGAUGUAACUGAAUGAAAUGGUGAAGGACGGGUCCAUGUCACACUCCAUGCUUCGGCA | hsa_miR-122 | UGGAGUGUGACAAUGGUGUUUG (SEQ ID NO.: 74) |
| 2643 | PNDN-hsa_let7f | GGGACACCUGAGUGUCCCACAACUAUACAUUGUUGAGUAGAGUGUGAGCUCCGUAACUAGUUACAUCACGGGAGAUGUAACUGAAUGAAAUGGUGAAGGACGGUCCACUACUACCUCAUGCUUCGGCA | hsa_let7f | UGAGGUAGUAGAUUGUAUAGUUGU (SEQ ID NO.: 2642) |
| 2645 | PNDN-dme-miR-124 | GGGACACCUGAGUGUCCCUUGGCAUUCUUGUUGAGUAGAGUGUGAGCUCCGUAACUAGUUACAUCACGGGAGAUGUAACUGAAUGAAAUGGUGAAGGACGGGUCCACGCGUGCCUUAGGCUGCUUCGGCAGCCUAAGGCACGCGGUGAAUGCCAA | dme-miR-124 | UAAGGCACGCGGUGAAUGCCAA (SEQ ID NO.: 2644) |
| 2647 | PNDN-dme-miR-14 | GGGACACCUGAGUGUCCCAUAGGAGAGAGUUGUUGAGUAGAGUGUGAGCUCCGUAACUAGUUACAUCACGGGAGAUGUAACUGAAUGAAAUGGUGAAGGACGGGUCCAAAAGACUGAGGCUGCUUCGGCAGCCUCAGUCUUUUUCUCUCUCCUAU | dme-miR-14 | UCAGUCUUUUUCUCUCUCCUAU (SEQ ID NO.: 2646) |
| 2649 | PNDN-dme-miR-184 | GGGACACCUGAGUGUCCCGCCCUUAUCUUGUUGAGUAGAGUGUGAGCUCCGUAACUAGUUACAUCACGGGAGAUGUAACUGAAUGAAAUGGUGAAGGACGGGUCCAUUCUCCGUCCAGGCUGCUUCGGCAGCC | dme-miR-184 | UGGACGGAGAACUGAUAAGGGC (SEQ ID NO.: 2648) |
| 2651 | PNDN-dme-miR-252 | GGGACACCUGAGUGUCCCUCCUGCGGCUUGUUGAGUAGAGUGUGAGCUCCGUAACUAGUUACAUCACGGGAGAUGUAACUGAAUGAAAUGGUGAAGGACGGGUCCAUAGUACUUAGGGCUGCUUCGGCAGCC | dme-miR-252 | CUAAGUACUAGUGCCGCAGGAG (SEQ ID NO.: 2650) |
| 2652 | PNDN_snoR442_5' | GGGACACCUGAGUGUCCCGAAUCACACCCUUGUUGAGUAGAGUGUGAGCUCCGUAACUAGUUACAUCACGGGAGAUGUAACUGAAUGAAAUGGUGAAGGACGGGUCCACAGGCUUGCGUGCUUCGGCA | snoR442 5' region | CGCAAGCCUGUUGGGUGUGAUUC (SEQ ID NO.: 2615) |
| 2654 | PNDN_snoR442_3' | GGGACACCUGAGUGUCCCGAUCAGAGUAUUGUUGAGUAGAGUGUGAGCUCCGUAACUAGUUACAUCACGGGAGAUGUAACUGAAUGAAAUGGUGAAGGACGGGUCCAUAUGACAAGCAUGCUUCGGCA | snoR442 3' region | UGCUUGUCAUAGUUACUCUGAUC (SEQ ID NO.: 2653) |

The underline (_____) sequence represents the sequence complementary to 3' end of the target RNA, the wavy underline (∿∿∿∿∿) sequence represents the sequence complementary to 5' end of the target RNA.

The isolated nucleic acid sequence of the first aspect can be used for the detection of a target nucleic acid sequence in an animal. Thus, in a second aspect, the present invention provides a method of detecting a target nucleic acid sequence in an animal, wherein the method comprises using the isolated nucleic acid sequence of the first aspect. In one example, the method comprises the steps of (i) contacting the isolated nucleic acid sequence of the first aspect with a detection agent and a sample obtained from the animal; and (ii) measuring the signal level from the detection agent.

The animal can be a mammalian animal or a non-mammalian animal. Examples of such animals include but are not limited to *Drosophila*, human, mouse, and zebra fish.

The term "sample" as used herein refers to a sample suspected of containing the target nucleic acid sequence. It may comprise a bodily fluid. The term "sample" used herein refers to a biological sample, or a sample that comprises at least some biological materials such as nucleic acids. The biological samples of this disclosure may be any sample suspected to contain the target nucleic acid sequence, including liquid samples, such as whole blood, blood serum, blood plasma, cerebrospinal fluid, central spinal fluid, lymph fluid, cystic fluid, sputum, stool, pleural effusion, mucus, pleural fluid, ascitic fluid, amniotic fluid, peritoneal fluid, saliva, bronchial washes, urine and other bodily fluid, or extracts thereof. It may also comprise an extract from a cell, chromosome, or organelle; genomic DNA, RNA, or cDNA.

In one example, the detecting of the target nucleic acid is in real-time.

The term "real-time" as used herein refers to the detection of the target nucleic acid sequence as the sequence is being produced, or the detection of the quantity of the target nucleic acid sequence as the quantity is changing with time. In some examples, the quantity of the target nucleic acid is increasing as it is being monitored, while in some other examples, the quantity of the target nucleic acid is decreasing as it is being monitored.

The target nucleic acid sequence to be detected can be a disease-specific nucleic acid sequence.

A large number of different target nucleic acid sequences can be detected using the isolated nucleic acid sequence of the first aspect, as the specific sequence of domains $C_1$ and $C_2$ can be designed based on the sequence of the target nucleic acid. Examples of the target nucleic acid sequences that can be detected include but not limited to the sequences of SEQ ID NO: 10 to 2597.

miRNAs are an emerging class of biomarkers, which are misregulated in a number of diseases. miRNA expression signatures (for example, up-regulations and down-regulations as compared to normal subject) have shown promise for use in diagnosis, staging of diseases, prognosis and as predictors of clinical response. For example, miRNA signatures correlate with neoplastic events, allowing early detection of cancer; circulating miRNAs have been detected patients with diffuse large B cell lymphoma. Therefore, method and systems for the detection and quantification of miRNAs have broad applicability.

Thus, in a third aspect, the present invention provides a method of determining if a subject has a disease or is at increased risk of developing a disease, wherein said method comprises providing a sample comprising nucleic acids from a subject and detecting one or more target nucleic acid sequences that bind to the isolated nucleic acid of the first aspect. In one example, the method comprises the steps of (i) contacting the isolated nucleic acid sequence of the first aspect with a detection agent and the sample from the subject; and (ii) measuring the signal level from the detection agent.

In a fourth aspect, the present invention provides a method of treating a patient which has a disease or is at increased risk of developing a disease, wherein said method comprises (i) providing a sample comprising nucleic acids from a patient and detecting one or more target nucleic acid sequences that bind to the isolated nucleic acid sequence of the first aspect, and (ii) administering to the patient one or more therapeutic agents for the treatment of the disease associated with the one or more target nucleic acid sequences detected in (i). In one example, steps (i) comprises (a) contacting the isolated nucleic acid sequence of the first aspect with a detection agent and the sample from the patient; and (ii) measuring the signal level from the detection agent.

Examples of such diseases include but are not limited to cardiac ischemia, diabetes, sepsis, rheumatoid arthritis, hepatic ischemia, hepatitis C, cardiac disease, Alzheimer's disease, Parkinson's disease, spinal motor neuron disease and cancer. Examples of cancer includes but are not limited to colorectal cancer, glioblastomas, neuroblastomas, acute myelogenous leukaemia, chronic lymphocytic leukaemia, lung cancer, non-small cell lung cancer, small cell lung cancer, B-cell lymphoma, T-cell lymphoma, multiple lymphoma, ovarian cancer, breast cancer, hepatocellular cancer, pancreatic cancer, prostate cancer and squamous cell carcinomas.

Currently available methods for determining if a patient has a disease or is at increased risk of developing a disease generally require complex biochemical processing and analysis of the sample. Such methods are thus time consuming, expensive, and require specialized skill set for analysis. In contrast, the methods of the third aspect could provide a fast and simple assay system suitable for use in the clinical laboratory without the need for advanced skills of the lab technicians.

In the fifth aspect, the present invention provides a kit comprising the isolated nucleic acid of the first aspect and a detection agent described herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1—Design and Preparation of Sensors

A fluorescent RNA-fluorophore complex, Spinach, has previously been used as a tag for mRNAs, and has also been adapted for use as sensors for small molecule metabolites screenings. The RNA scaffold of Spinach forms a binding site for a fluorophore, 3,5-difluoro-4-hydroxybenzylidene imidazolinone (DFHBI), which becomes fluorescent upon binding to the RNA scaffold.

Spinach2 is an aptamer that differs from Spinach by a few nucleotides, but is of a similar structure as the Spinach aptamer. Spinach2 is a single linear RNA molecule that was computationally predicted (mFold) to fold into a structure comprising four stem-loop regions (FIG. 6A). Spinach2 is brighter with better fluorescence properties as compared to Spinach. The crystal structure of Spinach2 when bound to the fluorophore DFHBI was then solved and shown to instead consist of a three-tetrad quadruplex flanked by two helices. The solved structure is diagrammed in simplified 2D form in FIG. 6B, and in detailed form in FIG. 6C. Although the strategy and experiments for the sensor design began with the mFold structure, prior to the publications of the crystal structure, for simplicity the experiments are illustrated in terms of the solved structure.

The inventors reasoned that a sensor with fluorescence properties similar to Spinach2 could be assembled from two different RNA molecules if the structural elements required for stable complex formation with DHFBI could be reconstituted by base pairing between these two RNA molecules. To make a bimolecular microRNA sensor, part of the structure of Spinach2 would have to be removed and replaced by sequences complementary to the miRNA, so that binding of the miRNA is required for stable complex formation. Sequences complementary to the miRNA in this duplex region could form the basis of a sensor. This would require two modifications: (i) to circularly permutate Spinach, changing the positions of the 5' and 3' ends of the RNA aptamer to reside within Stem-loop P3 (SL P3); and (ii) to introduce a second sequence-variable stem loop adjacent to SL P3. As the predicted mFold structure contained two stem loops adjacent to SL P3, a possible strategy was to alter one of them. Another strategy was to introduce a new stem-loop. The inventors systematically tested the modifications required for this approach to be feasible.

To produce a circularly permuted (CP) version of Spinach RNA, with the 5' end in SL P3, part of the T7 transcriptional start site needs to be incorporated into SL P3 without compromising fluorescence. Extending SL P3 by adding the partial T7 transcriptional start sequence GGGA did not reduce fluorescence (FIG. 7A, SL P3 T7). Using the T7 transcription start site in SL P3, the inventors synthesized a version of Spinach RNA in which the original 3' and 5' ends in stem P1 were connected with a short additional loop to produce a CP Spinach molecule. CP Spinach2 retained about 50% of the fluorescence of Spinach2 (FIG. 7A, CP Spinach2). An RNA in which the sequence of Spinach was randomly rearranged did not fluoresce (FIG. 7A, Scrambled Spinach2).

The CP Spinach design allowed for the possibility of a bimolecular sensor. To function, the sensor would require a second, adjacent stem loop whose sequence could also be varied. The inventors tested whether insertion of a new stem loop adjacent to Stem-loop P3 (SL P3) would be compatible with fluorescence. A second copy of the SL P3 sequence was inserted on the 5' side of the original SL P3 (FIG. 6A-C, grey arrow heads) or on the 3' side of the original SL P3 (FIG. 6A-C, black arrow heads). In both positions, this modification resulted in a functional fluorescent molecule (Dup SL P3, FIG. 7B). Next, the inventors tested adding a stem loop with a different sequence. This was well tolerated when inserted 3' to SL P3, but not when inserted at 5' to SL P3 (new SL P3 5', FIG. 7B). The inventors named the predicted three-stem loop fluorescent RNA-complex, Pandan (FIG. 8).

In short, the present inventors have redesigned Spinach so that folding to create a DFHBI-binding scaffold depends on interaction between a miRNA and a sequence complementary RNA backbone. This sensor family was named by the inventors as Pandan, after a plant used to provide an aromatic green coloring in Southeast Asian cooking. Binding of the target miRNA to the Pandan sensor reconstitutes an RNA structure capable of binding the DFHBI fluorophore in a manner similar to the Spinach2 aptamer. This novel aptamer serves as an RNA sensor that directly detects microRNAs by fluorophore binding.

Pandan sensors can be adapted for the detection of any miRNA. The sensors were designed by encoding complementary sequence for the 5' region of the target miRNA within Stem-loop P3 (SL P3), and the 3' region of the target miRNA within Stem-loop P4 (SL P4) of Pandan, with two unpaired nucleotides in the microRNA between the two portions. In some examples, the sensors were designed so that miRNA binding would result in a Uracil (U) in the second unpaired base downstream of SL P3. The online mFold server was then used to determine whether the sensor and miRNA pair were predicted to properly fold into the Pandan structure using a sequence where the sensor and miRNA were encoded as a single molecule.

The Pandan aptamer contains two adjacent stem loops (P3 and P4) that are essential for complex stability, but whose sequence can be varied. This structure allows the RNA portion of the RNA-fluorophore complex to be reconstituted by the binding of two separate RNA molecules, one of which can be any short RNA sequence.

Single stranded DNA templates for designed sensors (synthesized by Sigma Aldrich or IDT) were amplified using PCR to create double stranded DNA templates using primers that included a 5' T7 promoter sequence (5'-GTATAATACGACTCACTATAGGGA-3', SEQ ID NO: 9). PCR products were purified using PCR purification columns (Qiagen) and used as templates for in vitro T7 transcription (Epicentre) following the manufacturers' protocols. RNA sensors were extracted with ammonium acetate (5M) and phenolchloroform, and precipitated with isopropanol using standard procedures. RNA pellets were then suspended in nuclease-free water, their concentration measured on a Nanodrop instrument. Samples were stored at 80° C.

A specific RNA sensor is designed for each miRNA (or small RNA) by incorporating complementary sequence for the miRNA into the sensor backbone (FIG. 9B).

The sequence of the sensor backbone comprises: 5'-GGGACACCUGAGUGUCCCn-3' (SEQ ID NO: 1), wherein n of SEQ ID NO: 1 represents a sequence complementary to the target RNA and n of SEQ ID NO: 1 is attached to 5'-UUGUUGAGUAGAGUGUGAG-CUCCGUAACUAG UUACAUCACGGGAGAU-GUAACUGAAUGAAAUGGUGAAGGACGGGUCCn-3' (SEQ ID NO: 2658), wherein n of SEQ ID NO: 2658 represents a sequence complimentary to the target RNA and n of SEQ ID NO: 2658 is attached to 5'-GGCUGC-UUCGGCAGCC-3' (SEQ ID NO: 2659).

An example is given here for *Drosophila* miR-1 (In bold is the unpaired portion of the microRNA with the second unpaired base being a U):

```
Sequence of dme-miR-1
                                    (SEQ ID NO.: 4)
5'-UGGAAUGUAAAGAAGUAUGGAG-3'

Reverse complement of 3' paired seq
                                    (SEQ ID NO.: 5)
CUCCAUACUUCUUU Reverse complement of 5' paired seq
                                    (SEQ ID NO.: 6)
AUUCCA Foward primer:
                                    (SEQ ID NO.: 7)
GTATAATACGACTCACTATAGGGACACCTGAGTGTCC
CCTCCATACTTCTTTTTGTTGAGTAGAGTGTGAGCTC
Reverse primer:
                                    (SEQ ID NO.: 8)
GGCTGCCGAAGCAGCCTGGAATTGGACCCGTCCT
TCACCATTTCATTCAGT
```

Core template (can be used for all sensors):

(SEQ ID NO.: 2)
UUGUUGAGUAGAGUGUGAGCUCCGUAACUAGUUACAUCACGGGAGAUG
UAACUGAAUGAAAUGGUGAAGGACGGGUCCA.

Resulting sequence-specific sensor (sensor PNDN-dme-miR-1):

(SEQ ID NO.: 3)
GGGACACCUGAGUGUCCCCUCCAUACUUCUUUUUGUUGAGUAGAGUGU
GAGCUCCGUAACUAGUUACAUCACGGGAGAUGUAACUGAAUGAAAUGG
UGAAGGACGGGUCCAAUUCCAGGCUGCUUCGGCAGCC.

The predicted secondary structure of the designed RNA sensor is then checked using Mfold to ensure correct folding.

In vitro transcription of sensor from DNA template is carried out using Ampliscribe T7-Flash Transcription Kit (Epicenter) according to the manufacturer's instructions. The RNA is then purified by phenol/chloroform extraction and isopropanol precipitation.

Example 2—miRNA Detection by Sensor Fluorescence

The RNA sensor (1 µM), target miRNA (IDTDNA; variable concentrations) and DFHBI (10 µM; Lucerna Technologies) is incubated in solution with continuous shaking at 37° C. in buffer (40 mM HEPES pH 7.4, 125 mM KCl and 1 mM MgCl2) according to Paige et. al 2011 (Science 2011, (333) 642). Fluorescence is measured using a microplate reader (excitation wavelength 460 nm; emission wavelength 500 nm; slit widths 10 nm). Fluorescence measurement is then normalized to the maximum intensity of the fluorophore DFHBI alone.

Example 3—Pandan Sensors are Sensitive and Specific in Re Porting their MicroRNA of Interest Here, we show an example with Pandan-bantam-5p.
FIG. 2—Fluorescence fold change of Pandan-bantam-5p and DFHBI upon addition of 1 uM, 0.1 uM and 0.01 uM of bantam-5p microRNA, compared to DFHBI-only control.
FIG. 10B—The response of Pandan-bantam-5p to bantam-5p microRNA is linear.
FIG. 11A—Pandan-bantam-5p is specific for bantam-5p microRNA compared to miR-263a.

Example 4—Pandan Sensors Recognize MicroRNAs In Vitro

The sequences of both stem-loops P3 and the new additional stem-loop P4 can be varied. This allows the inventors to encode sequences complementary to target miRNAs into the Pandan sensor backbone (illustrated in FIG. 9B). Pandan sensors specific to *Drosophila* miRNAs dme-bantam-3p, dme-miR-263a and dme-miR-1000, as well as for several human miRNAs were designed.

RNA was extracted from 15-30 Canton S white (CS10) male flies using TRIzol reagent (Invitrogen) following the manufacturer's protocol. To detect target miRNA in this complex mixture of extracted RNA, synthetic target miRNA (1, 0.1 or 0.01 µM) (IDT), Pandan sensor (1 µM) and DFHBI or DFHBI-1T (10 µM) were added either to a solution of extracted RNA in a buffer containing 40 mM HEPES pH 7.4, 12 5 mM KCl and 1 mM MgCl2 or buffer control only without extracted RNA. Reactions were incubated at 37° C. for 1 h and fluorescence was recorded using a Tecan Safire2 fluorescence microplate reader with the following measurement parameters: excitation wavelength=460 nm; emission wavelength=501 nm; slit widths=10 nm. Experiments were carried out in triplicate for each data point.

In most cases, the sensor showed little or no fluorescence in the absence of the target miRNA. The fluorescence intensity of bound DFHBI increased between about 4- to 100-fold upon addition of target miRNA at 1 µM, compared to sensor or DFHBI alone (FIG. 11A). Fluorescence intensity increased with miRNA concentration (FIG. 11B), and the relationship was linear for the sensors that exhibited the brightest fluorescence: PNDN-bantam, PNDN-hsa-miR-21-5p, PNDN-hsa-let7f and PNDN-hsamiR-375 (FIG. 11B). The Pandan sensor PNDN-bantam-5p showed about 75% of the fluorescence intensity of Spinach2, on an equimolar basis, in the presence of its target miRNA (FIG. 11C).

Figure 3:
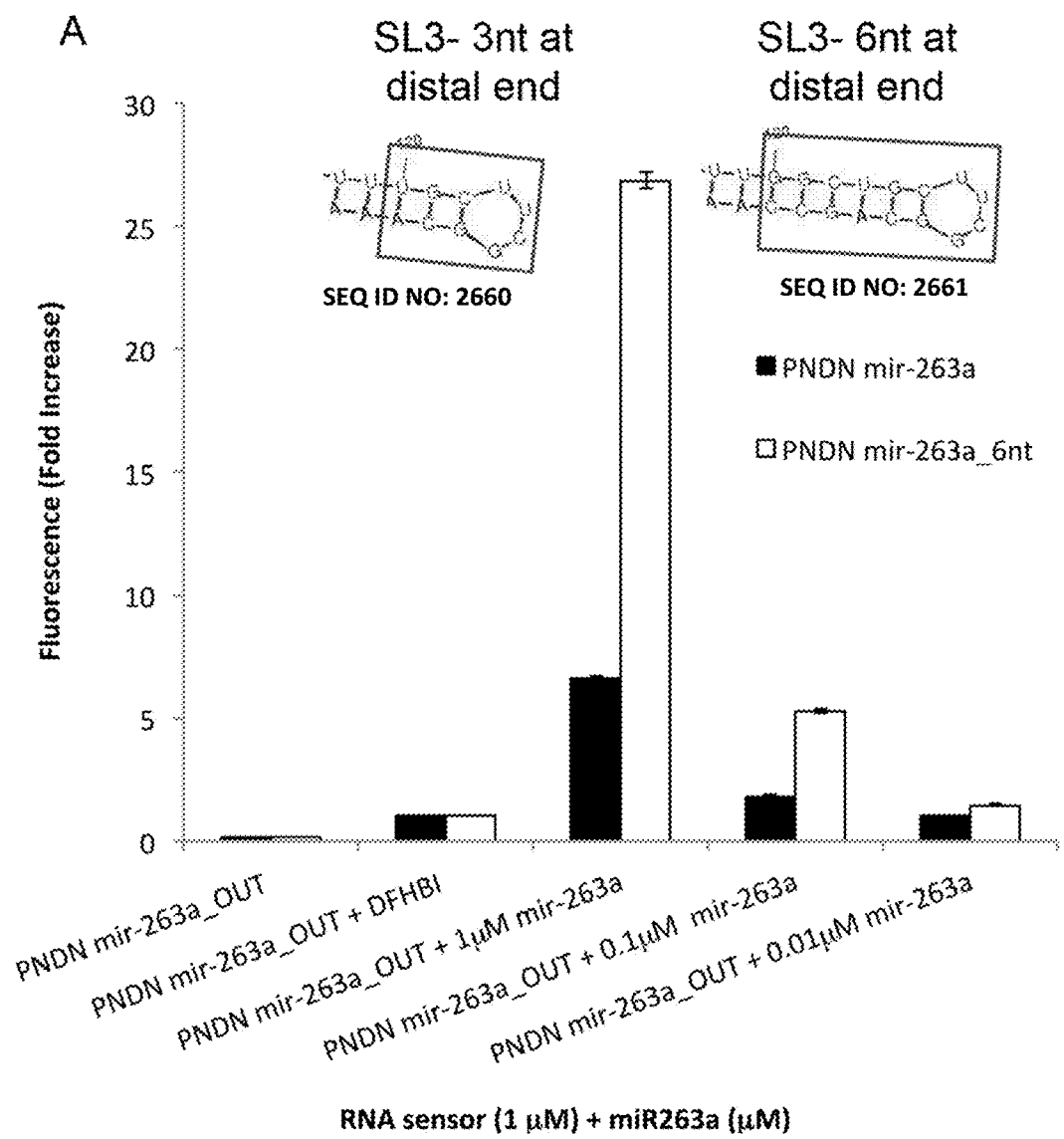
Figure 3:
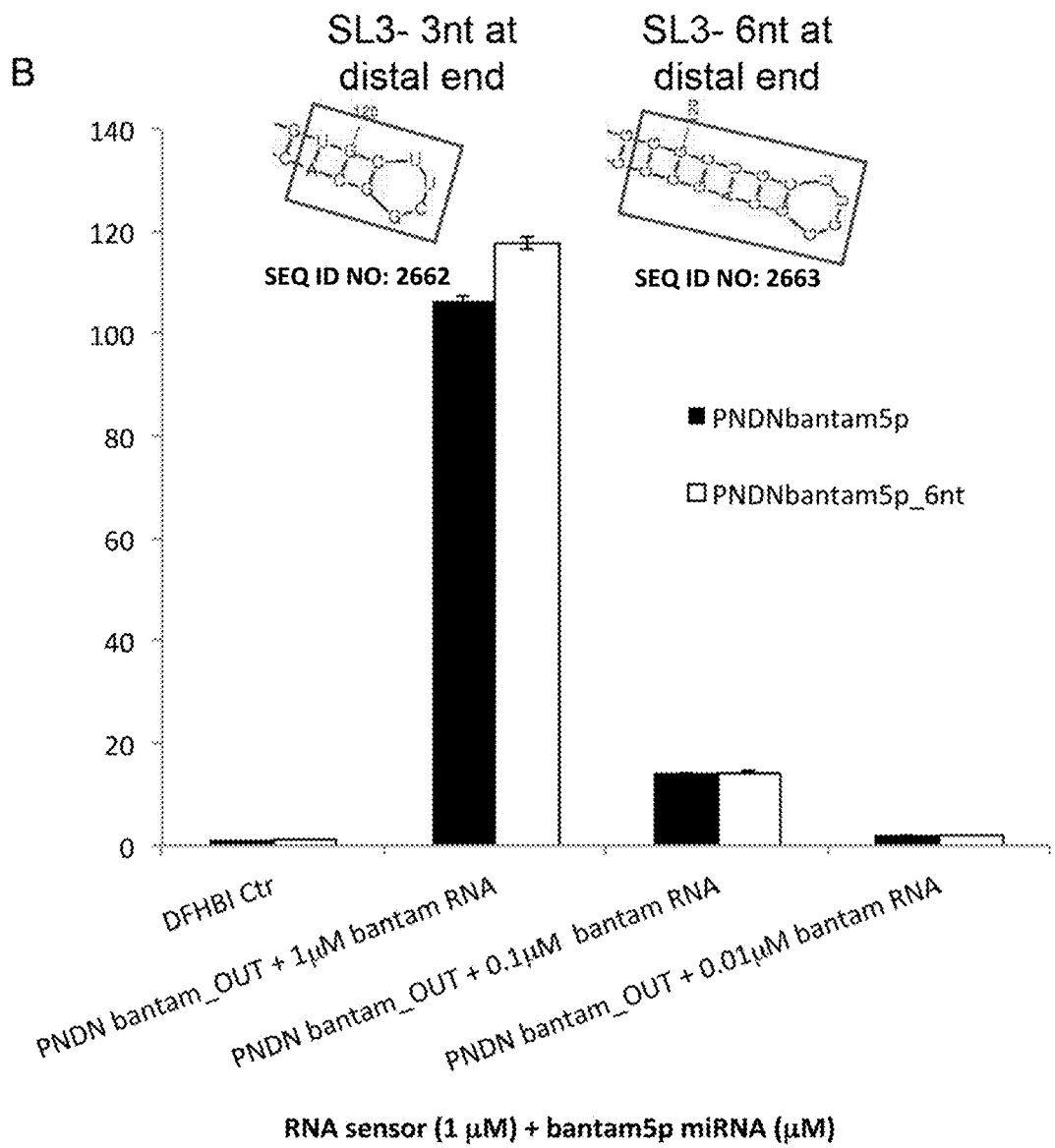
Figure 3:
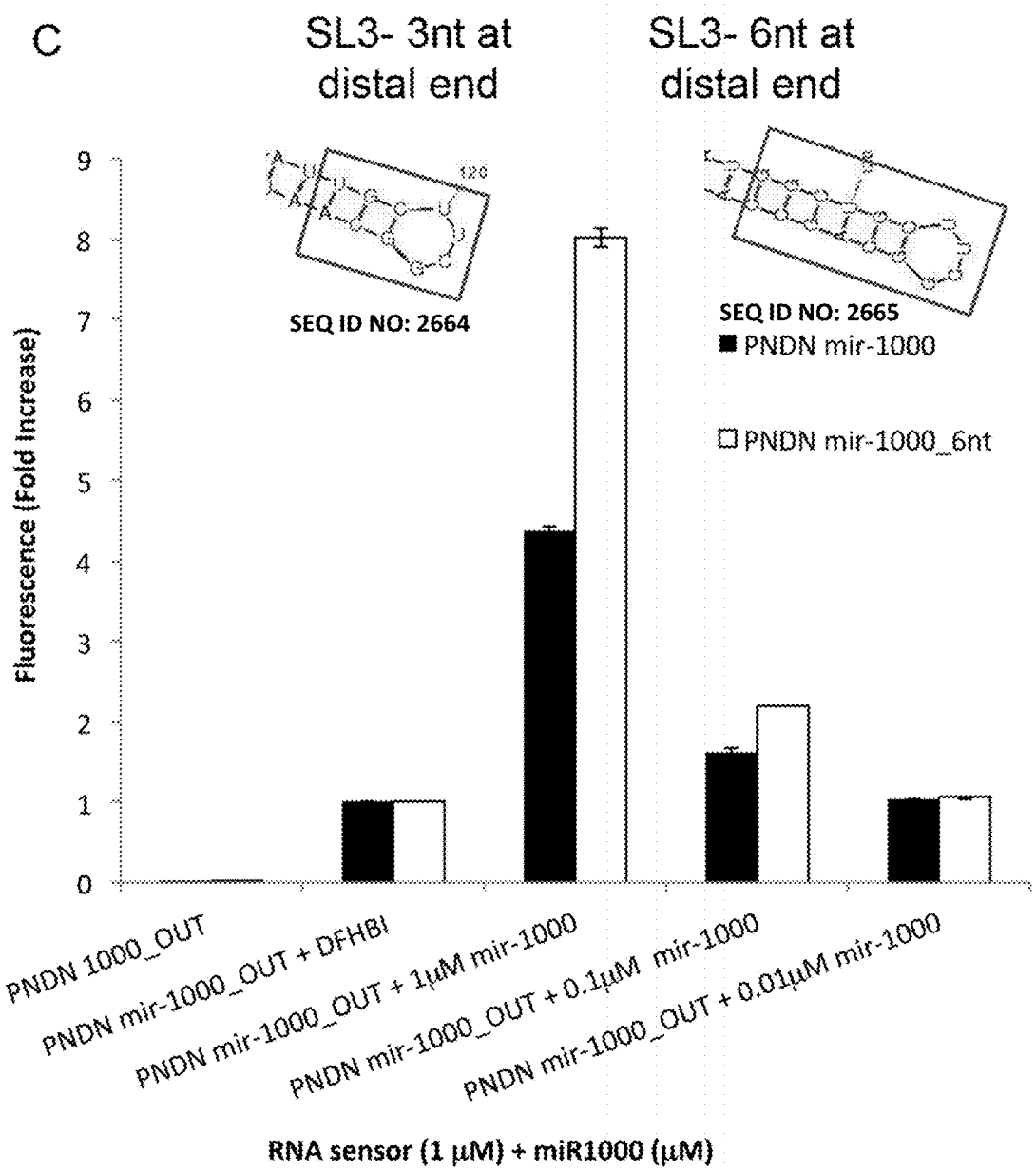
Figure 3:
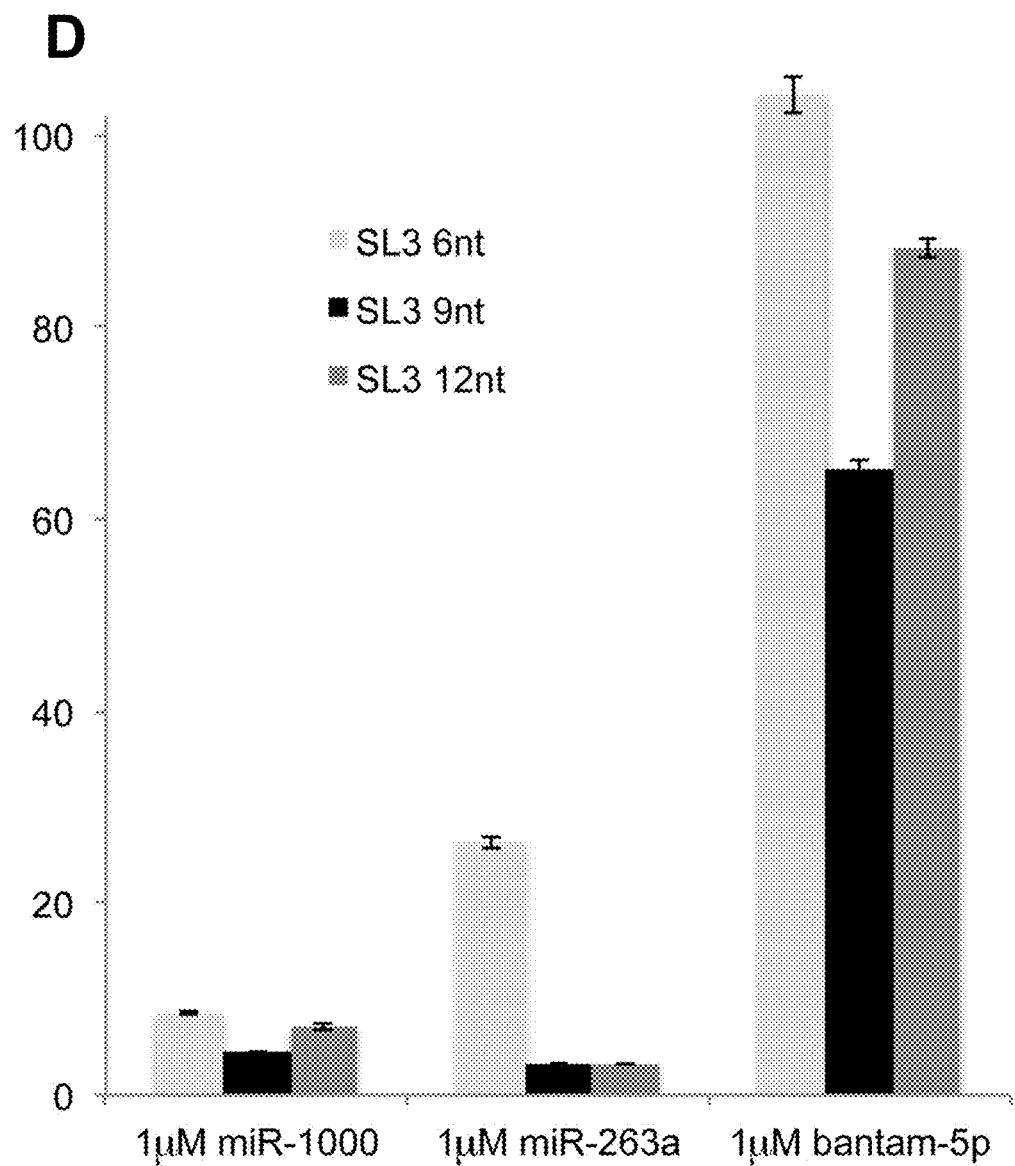
Figure 3:
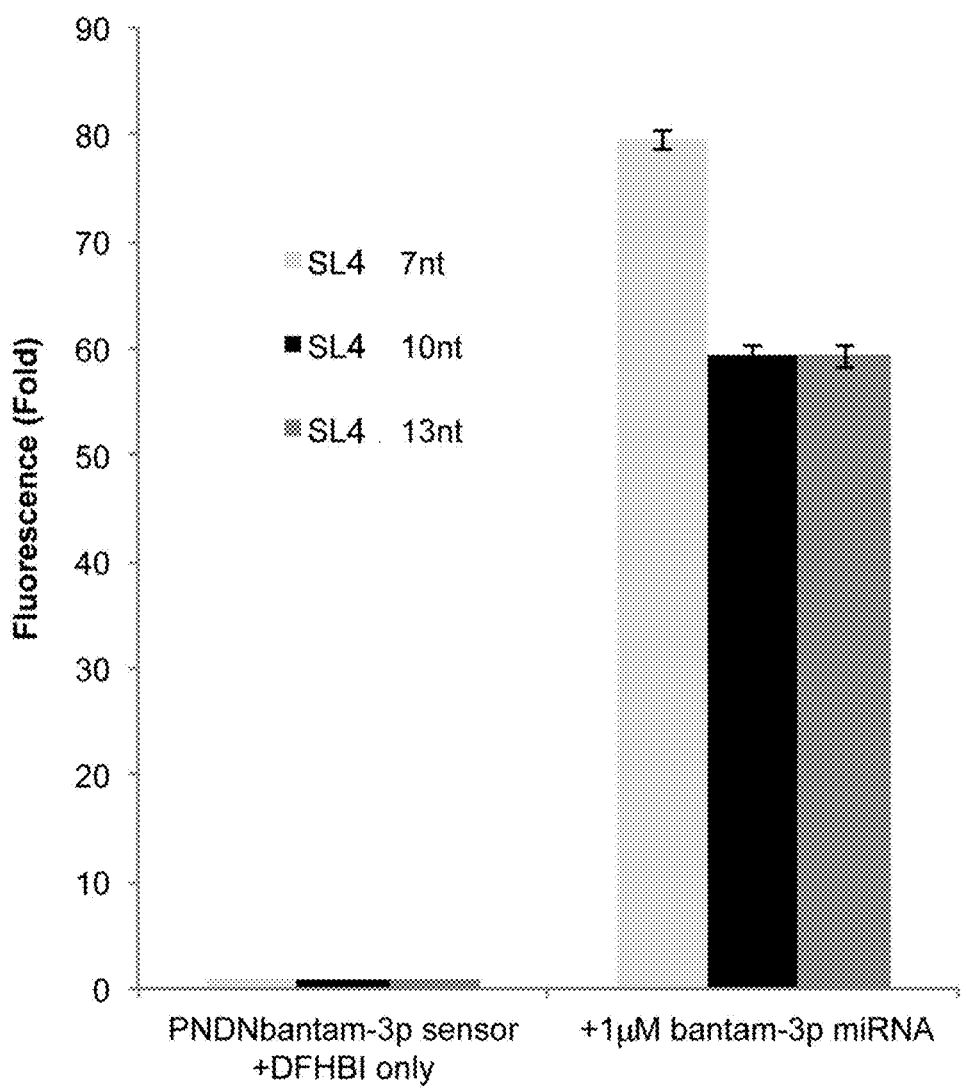
Figure 3:
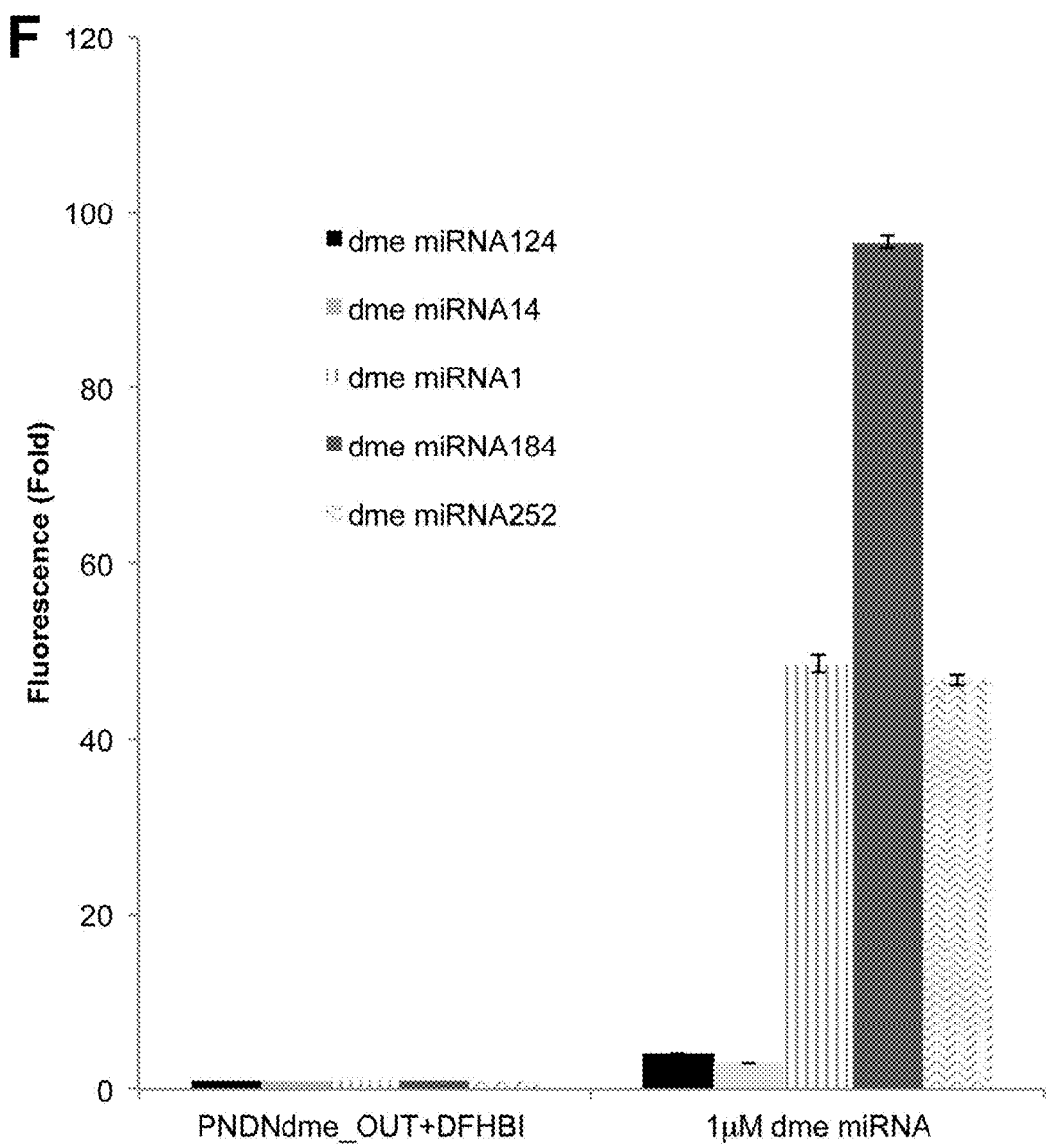

FIG. 3 presents tests of additional modifications to the basic sensor design. Extension of the self-pairing region of SL P3 from three to six residues improved low-sensitivity sensors: PNDN-miR-263a increased from about 7- to 27-fold and PNDN-miR-1000 from about 4- to about 8-fold, while having less impact on those that were already sensitive (FIG. 3A to C). Further extension of SL P3 did not further improve sensor signal (FIG. 3D). Extension of stem loop P4 did not improve sensor signal (FIG. 3E). Five additional *Drosophila* miRNA sensors with the extended P3 design showed fluorescence increases from about 3- to about 96-fold upon miRNA addition (FIG. 3F). The median increase in fluorescence was 49-fold for the 14 Pandan miRNA sensors tested (Table 2).

In some examples, the sensors were designed so that miRNA binding would result in a uracil (U) in the second nucleotide downstream of SL P3 (FIGS. 8 and 9B). The sensors tested function well when complementary sequences for at least 6 nucleotides on both ends of the miRNA are encoded in the sensor (e.g. dme-miR-1, Table 2). About 89% of all human miRNAs have a Uracil located at the 3' unpaired base, such that this Uracil residue is flanked by at least 6 nucleotides on both sides.

Example 5—Sequence Specificity

The inventors next investigated the sequence specificity of Pandan sensors. Addition of miR-263a to the bantam-5p-Pandan sensor in the presence of DFHBI did not increase its fluorescence (FIG. 11A). Nor did miR-263a reduce the sensitivity of this sensor to bantam-5p miRNA when the two miRNAs were added in equal concentrations. Similar results were obtained when probing the miR-1000 Pandan sensor with bantam-5p miRNA (FIG. 11A). Thus, Pandan sensors distinguish between miRNAs with dissimilar sequences.

Next, sequence changes were introduced into the test miRNAs to assess the ability of the sensors to differentiate between more closely related sequences. Changing three residues in the 5' arm of the miRNA strongly reduced sensor fluorescence for the three examples tested (FIG. 11B). Single nucleotide mismatches in the miRNA seed reduced bantam-5p sensor activity by about 20-50%, with the magnitude of the difference being somewhat dependent on the location of the mismatch (FIG. 11C).

For Pandan sensors to be useful for detecting miRNAs in biological samples, the sensor must be able to identify its target RNA in a complex mixture. To test this, total RNA from adult *Drosophila* were prepared and assayed the ability of the bantam-3p Pandan sensor to detect bantam-3p miRNA spiked into the RNA mixture at a range of concentrations. The presence of up to 1000-fold excess of competing RNA did not decrease the ability of bantam-3p sensor to detect bantam-3p (P>0.05; FIG. 11D).

TABLE 2

Raw fluorescence readings in arbitrary units (a.u.) for each of the tested sensors in the absence and presence of 1 μM target miRNA

| microRNA | # self-paired bases at 3' end of SL P3 | Sensor + DFHBI alone | Sensor + DFHBI + miRNA | Fold change |
|---|---|---|---|---|
| dme-bantam-5p | 6 | 395 | 46 464 | 118 |
| dme-bantam-5p | 3 | 434 | 46 278 | 107 |
| dme-miR-184 | 6 | 398 | 38 426 | 97 |
| dme-bantam-3p | 3 | 457 | 43 279 | 95 |
| hsa-miR21-5p | 3 | 425 | 29 018 | 68 |
| hsa-let7f | 3 | 553 | 36 679 | 66 |
| hsa-miR223-5p | 3 | 416 | 24 869 | 60 |
| hsa-miR375 | 3 | 443 | 25 957 | 59 |
| hsa-miR122 | 3 | 424 | 20 706 | 49 |
| dme-miR-1 | 6 | 406 | 19 720 | 49 |
| dme-miR-252 | 6 | 991 | 46 368 | 47 |
| dme-miR-263a | 6 | 416 | 11 172 | 27 |
| hsa-miR223-3p | 3 | 1518 | 20 756 | 14 |
| dme-miR-1000 | 6 | 3343 | 26 788 | 8 |

TABLE 2-continued

Raw fluorescence readings in arbitrary units (a.u.) for each of the tested sensors in the absence and presence of 1 μM target miRNA

| microRNA | # self-paired bases at 3' end of SL P3 | Sensor + DFHBI alone | Sensor + DFHBI + miRNA | Fold change |
|---|---|---|---|---|
| dme-miR-263a | 3 | 437 | 2903 | 7 |
| dme-miR-1000 | 3 | 5708 | 24 981 | 4 |
| dme-miR-124 | 6 | 10 522 | 41 931 | 4 |
| dme-miR-14 | 6 | 4708 | 14 175 | 3 |

Example 6—Pandan Sensors Detect Longer RNAs

Figure 5:
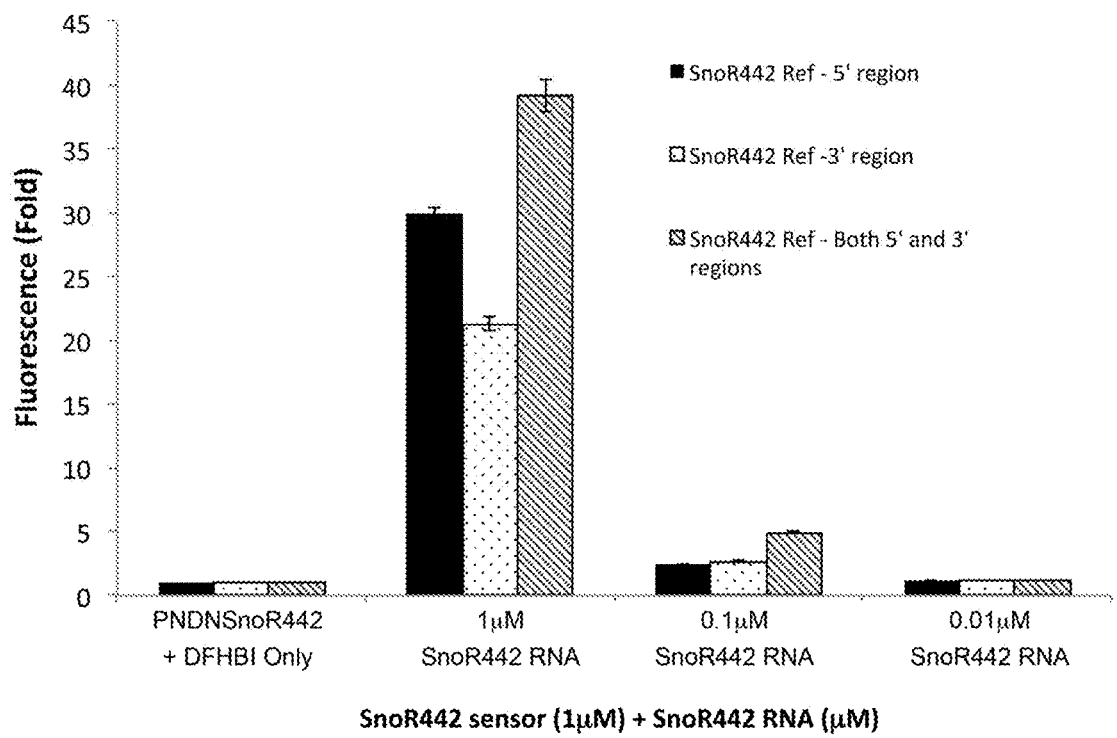

The Pandan sensors described above were designed to allow pairing to the entire 19-23 nucleotides of their respective target miRNAs. To explore whether sensors of this design could be used to detect longer RNA molecules, sensors were prepared for the 46-nt SnoR442 RNA. Pandan sensors complementary to the 5' or 3' 23-nt halves of SnoR442 were designed (FIG. 5). Both sensors were able to detect SnoR422. The extended unpaired sequence of the target does not appear to compromise sensor binding at either the 5' or 3' end. Combining the two sensors had an additive effect on raw fluorescence values, and increased fold fluorescence to a moderate degree (FIG. 5).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11174505B2). An electronic copy of the "Sequence Listing" will also be available from the USPTO upon request and payment of the fee set forth in 37 CFR 1.19(b)(3).

What is claimed is:

1. An isolated nucleic acid molecule for detecting the presence of a target nucleic acid sequence, wherein the isolated nucleic acid molecule comprises the following structure:

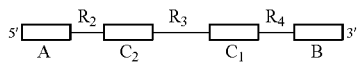

wherein each of A and B is a domain forming a stabilizing secondary structure within the domain, wherein C1 and C2 are domains that bind to the target nucleic acid sequence, wherein R2 and R4 are regions of nucleic acids that do not bind with the target nucleic acid sequence, and wherein R3 is a region of nucleic acids capable of stabilizing a detection agent upon the isolated nucleic acid molecule binding to the target nucleic acid sequence,
wherein the stabilizing secondary structure is selected from the group consisting of stems, stem loops, t-RNA type structures, cloverleaves, tetraloops, pseudoknots and combinations thereof,
wherein $R_3$ comprises a fluorophore binding pocket comprising a G-quadruplex region and a UAU base triple,
wherein the fluorophore binding pocket, the G-quadruplex region, and the UAU base triple are destabilized in the absence of the target nucleic acid sequence,
wherein the detection agent is a fluorophore that binds to the stabilized fluorophore binding pocket of $R_3$, and
wherein the isolated nucleic acid molecule is an RNA sequence.

2. The isolated nucleic acid molecule of claim 1, wherein the structure further comprises regions $R_1$ and $R_5$, wherein $R_1$ is upstream from domain A and $R_5$ is downstream from domain B, wherein $R_1$ and $R_5$ are regions of nucleic acids that do not bind with the target nucleic acid sequence, and wherein $R_1$ is a region capable of forming a secondary structure within the $R_1$ region and $R_5$ is a region capable of forming a secondary structure within the $R_5$ region.

3. The isolated nucleic acid molecule of claim 1, wherein $R_2$ is a region capable of forming a secondary or linear structure within the $R_2$ region and $R_4$ is a region capable of forming a secondary of linear structure within the $R_4$ region.

4. The isolated nucleic acid molecule of claim 3, wherein the secondary structure is selected from the group consisting of stems, stem loops, t-RNA type structures, cloverleaves, tetraloops, pseudoknots and combinations thereof.

5. The isolated nucleic acid molecule of claim 1, wherein domain A forms a stem loop within the domain A and domain B forms a stem loop within the domain B.

6. The isolated nucleic acid molecule of claim 5, wherein the stem of the stem loop formed within the domain A is independently 6 or 7 nucleotide base-pairs long and wherein the stem of stem loop formed within the domain B is independently 6 or 7 nucleotide base-pairs long.

7. The isolated nucleic acid molecule of claim 1, wherein the nucleic acids of domains $C_1$ and $C_2$ complementarily bind to the 5' and 3' ends of the target nucleic acid sequence.

8. The isolated nucleic acid molecule of claim 1, wherein domain $C_1$ is 9-13 nucleotides in length or wherein domain $C_2$ is 9-13 nucleotides in length.

9. The isolated nucleic acid molecule of claim 1, comprising a combination comprising SEQ ID NO: 1, followed by SEQ ID NO: 2658, followed by SEQ ID NO: 2659.

10. The isolated nucleic acid molecule of claim 1, comprising the sequence selected from the group consisting of SEQ ID NO: 3, SEQ ID NO: 5, SEQ ID NO: 6 and combinations thereof.

11. The isolated nucleic acid molecule of claim 1, comprising the sequence selected from the group consisting of SEQ ID NOs: 2618 to 2632, 2634, 2636, 2638, 2640, 2641, 2643, 2645, 2647, 2649, 2651, 2652 and 2654.

12. The isolated nucleic acid molecule of claim 1, wherein the target nucleic acid sequence is an RNA sequence or a miRNA sequence.

13. The isolated nucleic acid molecule of claim 12, wherein the target nucleic acid sequence is a miRNA sequence.

14. A kit comprising:
an isolated nucleic acid molecule for detecting the presence of a target nucleic acid sequence, wherein the isolated nucleic acid molecule comprises the following structure:

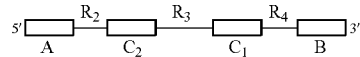

wherein each of A and B is a domain forming a stabilizing secondary structure within the domain, wherein C1 and C2 are domains that bind to the target nucleic acid sequence, wherein R2 and R4 are regions of nucleic acids that do not bind with the target nucleic acid sequence and wherein R3 is a region of nucleic acids capable of stabilizing a detection agent upon the isolated nucleic acid molecule binding to the target nucleic acid sequence, wherein the stabilizing secondary structure is selected from the group consisting of stems, stem loops, t-RNA type structures, cloverleaves, tetraloops, pseudoknots and combinations thereof, wherein $R_3$ comprises a fluorophore binding pocket comprising a G-quadruplex region and a UAU base triple, wherein the fluorophore binding pocket, the G-quadruplex region, and the UAU base triple are destabilized in the absence of the target nucleic acid sequence, wherein the isolated nucleic acid molecule is an RNA sequence; and wherein the detection agent is a fluorophore that binds to the stabilized fluorophore binding pocket of $R_3$.

* * * * *